(12) United States Patent
Niedzwiecki et al.

(10) Patent No.: US 11,654,131 B1
(45) Date of Patent: *May 23, 2023

(54) COMPOSITION AND METHOD OF TREATMENT OF HEALTH ISSUES RELATED TO ESTROGEN METABOLISM WITH ELEVATED RISK FACTORS IN FEMALES

(71) Applicant: Matthias W Rath, Henderson, NV (US)

(72) Inventors: Aleksandra Niedzwiecki, Henderson, NV (US); Matthias W Rath, Henderson, NV (US); Parthena Boulikas, Sanjose, CA (US); Anna Goc, Sanjose, CA (US); Gabriela Lopez, Oakland, CA (US)

(73) Assignee: Matthias W. Rath, Henderson, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/966,901

(22) Filed: Oct. 17, 2022

Related U.S. Application Data

(60) Provisional application No. 63/338,043, filed on May 4, 2022.

(51) Int. Cl.
| | |
|---|---|
| *A61K 31/375* | (2006.01) |
| *A61P 35/00* | (2006.01) |
| *A61K 31/355* | (2006.01) |
| *A61K 31/197* | (2006.01) |
| *A61K 31/675* | (2006.01) |
| *A61K 31/519* | (2006.01) |
| *A61K 33/18* | (2006.01) |
| *A61K 33/04* | (2006.01) |
| *A61K 31/14* | (2006.01) |
| *A61K 31/047* | (2006.01) |
| *A61K 31/685* | (2006.01) |
| *A61K 31/353* | (2006.01) |
| *A61K 36/48* | (2006.01) |
| *A61K 36/537* | (2006.01) |
| *A61K 36/53* | (2006.01) |
| *A23L 33/15* | (2016.01) |
| *A23L 33/16* | (2016.01) |
| *A23L 33/125* | (2016.01) |
| *A23L 33/105* | (2016.01) |
| *A61P 5/24* | (2006.01) |

(52) U.S. Cl.
CPC .......... *A61K 31/375* (2013.01); *A23L 33/105* (2016.08); *A23L 33/125* (2016.08); *A23L 33/15* (2016.08); *A23L 33/16* (2016.08); *A61K 31/047* (2013.01); *A61K 31/14* (2013.01); *A61K 31/197* (2013.01); *A61K 31/353* (2013.01); *A61K 31/355* (2013.01); *A61K 31/519* (2013.01); *A61K 31/675* (2013.01); *A61K 31/685* (2013.01); *A61K 33/04* (2013.01); *A61K 33/18* (2013.01); *A61K 36/48* (2013.01); *A61K 36/53* (2013.01); *A61K 36/537* (2013.01); *A61P 5/24* (2018.01); *A61P 35/00* (2018.01); *A23V 2002/00* (2013.01)

(58) Field of Classification Search
CPC .... A61K 31/375; A61K 31/047; A61K 31/14; A61K 31/197; A61K 31/353; A61K 31/355; A61K 31/519; A61K 31/675; A61K 31/685; A61K 33/04; A61K 33/18; A61K 36/48; A61K 36/53; A61K 36/537; A23L 33/105; A23L 33/125; A23L 33/15; A23L 33/16; A61P 5/24; A61P 35/00; A23V 2002/00

See application file for complete search history.

*Primary Examiner* — Jessica Worsham
(74) *Attorney, Agent, or Firm* — Geeta Kadambi; Riddhi IP LLC

(57) ABSTRACT

A basic mix or Mix 1 or Mix 2 is highly effective in treating estrogen related complications in females. The estrogen related diseases such as cancer are also treated if they are Apo E based manifestations. The basic mix or Mix 1 or Mix 2 comprises of a combination of a Vitamin C (Ca ascorbate) 10 mg-100,000 mg, Vitamin E (D-alpha-tocopherol) 1-3,000 mg, Vitamin B5 1-20,000 mg, Vitamin B6 1-1,000 mg, Folic acid 1-3,000 mcg, Iodine (Kelp) 1-2,000 mcg, Selenium 1-2,000 mcg, Choline 1-5,000 mg, Inositol 1-5000 mg, Phosphatidyl serine 1-1,500 mg, Daidzein 1-1,500 mg, Glycitein 0.1-1,000 mg, Genistein 1-2,500 mg, Red clover 1-1,500 mg, Rosemary extract 1-6,000 mg and Chaste tree berry (*Vitex agnus*-castus) 1-2,000 mg. The treatment by administering Mix 1 decreases estrogen dependent breast cancer cells proliferation and decrease in expression of cancer promoting cellular markers in cancer cells (iNOS, ApoE).

12 Claims, 17 Drawing Sheets

COMPOSITION AND METHOD OF TREATMENT OF HEALTH ISSUES RELATED TO ESTROGEN METABOLISM WITH ELEVATED RISK FACTORS IN FEMALES

CROSS REFERENCE TO RELATED APPLICATION

This application claims priority to U.S. Provisional application 63/338,043 filed May 4, 2022. The U.S. Provisional Application 63/338,043 is hereby incorporated by reference in its entireties for all of its teachings.

FIELD OF STUDY

This application discloses a micronutrient mixture and method of treating estrogen related complications using the micronutrient mixture in mammal.

BACKGROUND

Oxidative stress is highly pathogenic and associated with numerous diseases, including female reproductive diseases and impairing fertility. Oxidative damage can affect variety of physiological mechanisms such as oocyte maturation, fertilization, implantation, embryo development and hence contributes to the pathophysiology of pregnancy related complications, endometriosis, polycystic ovarian disease, unexplained infertility and gynecological cancers. Various antioxidant vitamins and supplements have been recommended to balance pro-oxidant and anti-oxidant cellular processes, but efficacy of their combinations is rarely evaluated. There is a need for sustained long effective treatment regimen to mitigate chronic disease such as arthritis.

Women have special requirements for nutrients, which vary over their lifetime. Common perception that diet assures all nutritional needs of their body is not correct. While good nutrition is the basis of health, commercial agriculture and food preparation deplete our food many vital ingredients which makes even healthy diet inadequate in providing optimum supply of vitamins and other micronutrients. This is especially important when health challenges and physiological transitions in a woman body require specific adjustments in the amounts and types of beneficial micronutrients. Therefore, properly selected nutritional supplementation is essential.

SUMMARY

The instant micronutrient mixture is comprised of basic mix or Mix 1 or Mix 2 that prevents, treats and delays estrogen related complications in mammal, specifically in females. In one embodiment, micronutrient mixture is comprised of basic mix or Mix 1 or Mix 2 and are formulated and tested in human cells to treat estrogen related complications. In another embodiment, all micronutrient mixtures were evaluated for their efficacy in various cellular metabolic aspects related to female metabolism. A micronutrient mixture is a Vitamin C in ascorbate form, Vitamin E in D-alpha-tocopherol form, Vitamin B5, Vitamin B6, Folic acid, Iodine (Kelp), Selenium, Choline, Inositol, Phosphatidyl serine, Daidzein, Glycitein, Genistein, Red clover, Rosemary extract, Chaste tree berry and optionally adding one or combination of pharmaceutically acceptable carriers or excipient or liquefied propellant or buffer or pH regulator or stabilizer or coating or flavoring agent is formulated as a tablet, coated tablet, capsule, pill, intranasal, lozenges, emulsion, pastilles, suppository, paste or injectable solution In another embodiment, Mix 1 comprises of Vitamin C (Ca ascorbate) 10 mg-100,000 mg, Vitamin E (D-alpha-tocopherol) 1-3,000 mg, Vitamin B5 1-20,000 mg, Vitamin B6 1-1,000 mg, Folic acid 1-3,000 mcg, Iodine (Kelp) 1-2,000 mcg, Selenium 1-2,000 mcg, Choline 1-5,000 mg, Inositol 1-5000 mg, Phosphatidyl serine 1-1,500 mg, Daidzein 1-1,500 mg, Glycitein 0.1-1,000 mg, Genistein 1-2,500 mg, Red clover 1-1,500 mg, Rosemary extract 1-6,000 mg and Chaste tree berry (*Vitex agnus*-castus) 1-2,000 mg. In another embodiment, micronutrient mixture that consists of a basic mix or Mix 1 or Mix 2 which a combination of a Vitamin C in ascorbate form, Vitamin E in D-alpha-tocopherol form, Vitamin B5, Vitamin B6, Folic acid, Iodine (Kelp), Selenium, Choline, Inositol, Phosphatidyl serine, Daidzein, Glycitein, Genistein, Red clover, Rosemary extract, Chaste tree berry and optionally adding one or combination of pharmaceutically acceptable carriers or excipient or liquefied propellant or buffer or pH regulator or stabilizer or coating or flavoring agent is formulated as a tablet, coated tablet, capsule, pill, intranasal, lozenges, emulsion, pastilles, suppository, paste or injectable solution. In another embodiment, micronutrient mixture is comprising of a basic mix, Mix 1 or Mix 2 are administered in human specifically female for improving, protecting and mitigating their estrogen related maladies.

In another embodiment the basic mix, Mix 1 and Mix 2 enhances healthy metabolism by increasing bioenergy (ATP) production, hormonal support by enhancing estrogen and progesterone synthesis and antioxidant protection of the body cells. In one embodiment, unexpected and superior results showed alleviating risk of female gender related pathologies such as in cancer patients decreasing estrogen dependent breast cancer cells proliferation and decrease in expression of cancer promoting cellular markers in lung cancer cells (iNOS, ApoE) or other organ cancers.

In one embodiment, administering the basic mix or Mix 1 or Mix 2 in females for enhancing healthy metabolism in females at different stages of life is described. Method of treating estrogen related female health issues by administering the basic mix or Mix 1 or Mix 2 in females is described. The formulated doses of the basic mix or Mix 1 or Mix 2 in females are also calculated based on physiological conditions for optimal absorbency and bioavailability specific to method of treatment, mode of administering and dosage based on condition of the female recipient.

Finally, the present invention is described further in the detailed description to further illustrate various aspects of the present invention.

BRIEF DESCRIPTION OF DRAWINGS

Example embodiments are illustrated by way of example only and not limitation, with reference to the figures of the accompanying drawings, in which like references indicate similar elements and in which.

Figure 1:
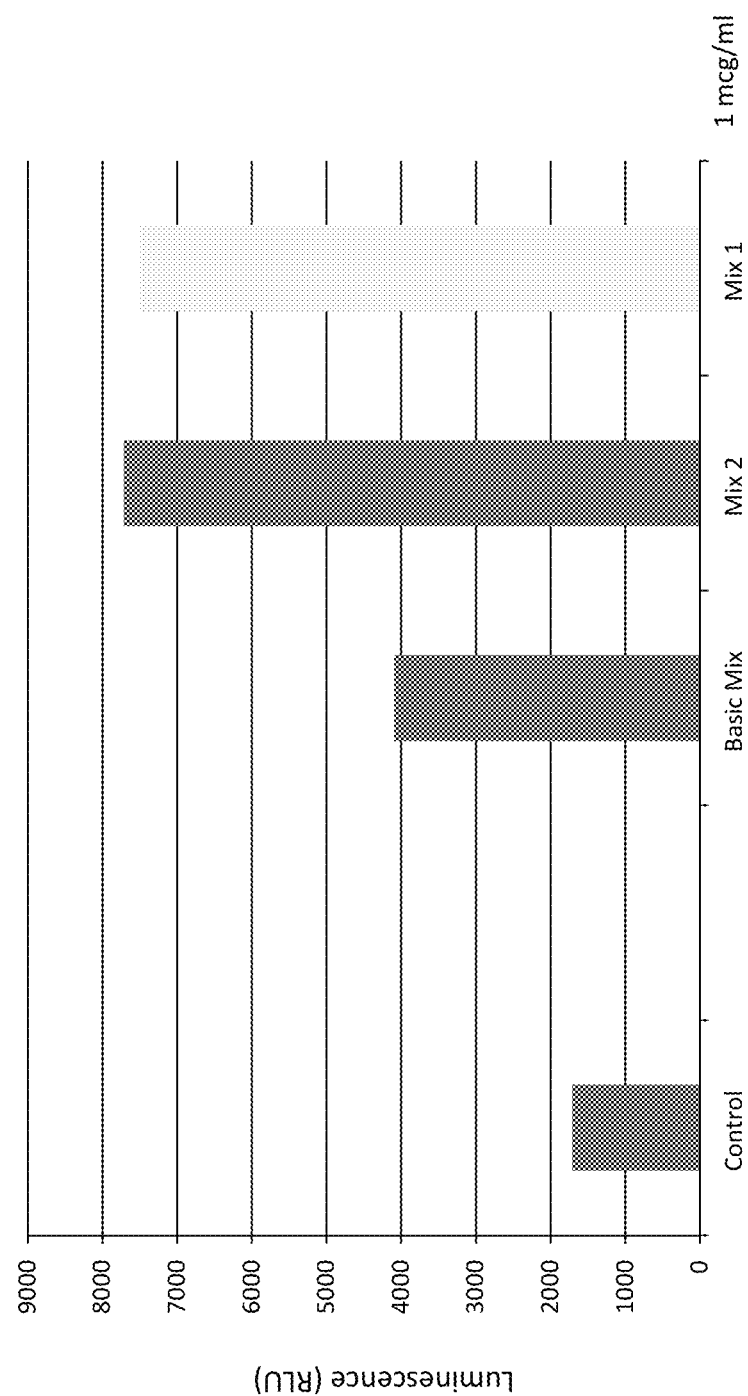
FIG. 1: Effects of micronutrient mixtures: Basic Mix, Mix 1 and Mix 2 on ATP synthesis in cardio myoblasts was studied.

Other features of the present disclosure will be apparent from the accompanying drawings and from the detailed description of embodiments that follows.

DETAILED DESCRIPTION

Micronutrients are essential for life, for maintaining hormonal balance, optimum immunity, cell protection, and maintaining normal psychological health. The most effective way to assure health benefits of micronutrients is by supplementation with synergistic combinations of micronutrients with scientifically tested and proven efficacy. The present disclosure shows various combination of micronutrient mixture such as Vitamin C in ascorbate form, Vitamin E in D-alpha-tocopherol form, Vitamin B5, Vitamin B6, Folic acid, Iodine (Kelp), Selenium, Choline, Inositol, Phosphatidyl serine, Daidzein, Glycitein, Genistein, Red clover, Rosemary extract, Chaste tree berry and optionally adding one or combination of pharmaceutically acceptable carriers or excipient or liquefied propellant or buffer or pH regulator or stabilizer or coating or flavoring agent is formulated as a tablet, coated tablet, capsule, pill, intranasal, lozenges, emulsion, pastilles, suppository, paste or injectable solution to form basic mix or Mix 1 or Mix 2. The tables show the exact combinations in detail.

This disclosure stows exceptional results of a basic mix or Mix 1 or Mix 2 and method of treatment in estrogen related health issues in females. Several methods were used to prove the efficacy of the basic mix or Mix 1 or Mix 2. Oxidative stress is highly pathogenic and associated with numerous diseases, including female reproductive diseases and impairing fertility. Oxidative damage can affect variety of physiological mechanisms such as oocyte maturation, fertilization, implantation, embryo development and hence contributes to the pathophysiology of Pregnancy related complications, endometriosis, polycystic ovarian disease, unexplained infertility and gynecological cancers.

TABLE 1

Three Mixes composition for a single dose:

| Basic Mix | | Mix 1 | | Mix 2 | |
|---|---|---|---|---|---|
| Vitamin C (Ca ascorbate) | 250 mg | Vitamin C (Ca ascorbate) | 250 mg | Vitamin C (Ca ascorbate) | 250 mg |
| Vitamin E (D-alpha-tocopherol) | 60 mg | Vitamin E (D-alpha-tocopherol) | 60 mg | Vitamin E (D-alpha-tocopherol) | 60 mg |
| Vitamin B5 | 10 mg | Vitamin B5 | 10 mg | Vitamin B5 | 10 mg |
| Vitamin B6 | 8 mg | Vitamin B6 | 8 mg | Vitamin B6 | 8 mg |
| Folic acid | 100 mcg | Folic acid | 100 mcg | Folic acid | 100 mcg |
| Iodine (Kelp) | 100 mcg | Iodine (Kelp) | 100 mcg | Iodine (Kelp) | 100 mcg |
| Selenium | 25 mcg | Selenium | 25 mcg | Selenium | 25 mcg |
| Choline | 80 mg | Choline | 80 mg | Choline | 80 mg |
| Inositol | 80 mg | Inositol | 80 mg | Inositol | 80 mg |
| Phosphatidyl serine | 15 mg | Phosphatidyl serine | 15 mg | Phosphatidyl serine | 15 mg |
| Daidzein | 21 mg | Daidzein | 21 mg | Daidzein | 21 mg |
| Glycitein | 10.5 mg | Glycitein | 10.5 mg | Glycitein | 10.5 mg |
| Genistein | 3.75 mg | Genistein | 3.75 mg | Genistein | 3.75 mg |
| | | Red clover | 35 mg | Red clover | 35 mg |
| | | Rosemary extract | 50 mg | Rosemary extract | 50 mg |
| | | Chaste tree berry (Vitex agnus-castus Fruit) | 80 mg | | |

TABLE 2

Mix 1 composition as a range for various forms of administrations:

| | |
|---|---|
| Vitamin C (Ca ascorbate0- | 10 mg-100,000 mg |
| Vitamin E (D-alpha-tocopherol) | 1-3,000 mg |
| Vitamin B5 | 1-20,000 mg |
| Vitamin B6 | 1-1,000 mg |
| Folic acid | 1-3,000 mcg |
| Iodine (Kelp) | 1-2,000 mcg |
| Selenium | 1-2,000 mcg |
| Choline | 1-5,000 mg |
| Inositol | 1-5000 mg |
| Phosphatidyl serine | 1-1,500 mg |
| Daidzein | 1-1,500 mg |
| Glycytein | 0.1-1,000 mg |
| Genistein | 1-2,500 mg |
| Red clover | 1-1.500 mg |
| Rosemary extract- | 1-6,000 mg |
| Chaste tree berry (Vitex agnus-castus) | 1-2,000 mg |

Various antioxidant vitamins and supplements have been recommended to balance pro-oxidant and anti-oxidant cellular processes, but efficacy of their combinations is rarely evaluated. The formulations targets specific metabolic aspects associated with female metabolism in a complex way. By simultaneously enhancing Critical cellular mechanisms associated with healthy body functions and at the same time counteracting specific pathology markers with higher risks in female metabolism.

By applying nutrient synergy, the formulation can enhance individual metabolic processes compared to individual ingredients and at the same time can control several metabolic targets in a simultaneous way, such as maintaining hormonal balance, support bioenergy, alleviate markers associated with increased risk of breast and lung cancers. In one embodiment the ranges of ingredients in basic mix. Mix 1 and Mix 2 are from combinations of the following:

Vitamin C (calcium ascorbate) 10 mg-100,000 mg
Vitamin E (d-alpha tocopheryl succinate) 1-3,000 mg
Vitamin B6 1-1000 mg
Folate (L-methyltetrahydrofolate calcium) 0.1-4000 mcg
Pantothenic acid (vitamin B5) 1-1000 mg
Iodine (Kelp) 0.1-2000 mcg
Choline 1-5000 mg
Selenium L-selenomethionine) 1-5000 mcg
Inositol 1-5000 mg
Phosphatidyl serine (from sunflower) 1-5000 mg
SoyLife (soy extract) 40%* 1-5000 mg
Chaste tree fruit 1-2000 mg
Red clover flower 1-2000 mg
Rosemary leaf extract 1-6000 mg
Soy extract: Glycytein (0.1-1000 mg), Genistein (1-2500 mg), daidzein (1-1500 mg)

We used FRAP assay (ferric reducing ability of plasma) that has been applied to measure antioxidant capacity of food and evaluate antioxidant potential of various micronutrient mixtures. The assay is based on the reduction of ferric-tripyridyltriazine ($Fe^{3+}$-TPTZ) to an intense blue color ferrous-tripyridyltriazine complex ($Fe^{2+}$-TPTZ) with an absorption maximum at 593 nm. In this assay, trolox is mostly used as positive control and results are expressed as mM ferrous equivalents calculated from a standard curve.

MATERIALS and METHODS

Test ingredients: Basic formula from DRHP, Heerlen, NL, VITEX (Chaste) berry, powder *Vitex agnus*-castus (Monterey Bay Spice Company, 241 Walker St, Watsonville, Calif. 95076 USA), ROSEMARY EXTRACT (Powder City, 160 S Hartman St, York, Pa. 17403, USA), CLOVE extract 4:1 Powdered (NutriCargo LLC, 25 Main St. Building #6, Belleville, N.J., 07108, USA). The initial stock solutions for all test compounds were done in DMSO (20 mg/ml). Then, working dilutions were made in DMEM/10% FBS 1% PS (ATP measurements) or in Prigrow IV 10% FBS 5% Cosmic Calf Serum 1% PS (for 17 beta Estradiol).

FBS (Fetal Bovine serum Premium Select from R&D systems a bio-techne brand, 4172 Industry Way, Flowery Branch, Ga. 30542, USA); Penicillin Streptomycin and Trypsin-EDTA from Gibco; PBS (R&D systems a bio-techne brand, 4172 Industry Way, Flowery Branch, Ga. 30542, USA). Abcam detection kit ab108667 was used for 17 beta estradiol assay.

For 17 beta estradiol: PriCoat™-T75 Flasks (ABM Applied Biological Materials Inc., 1-3671 Viking Way, Richmond, BC, Canada V6V 2J5); Prigrow IV medium (ABM Applied Biological Materials Inc., 1-3671 Viking Way, Richmond, BC, Canada V6V 2J5; Applied Cell Extracellular Matrix (ABM Applied Biological Materials Inc., 1-3671 Viking Way, Richmond, BC, Canada V6V 2J5); Calf Serum Iron-Supplemented from R&D systems a bio-techne brand, 4172 Industry Way, Flowery Branch, Ga. 30542, USA)

For ATP determination: 96 well Assay, white, flat bottom plate, polystyrene (Corning Inc., 2 Alfred Rd, Kennebunk Me. 04043, USA). All other reagents were provided in respective test kits by the manufacturers or purchased from Sigma-Aldrich.

Cell Cultures:
HGL5 (Immortalized Human Ovarian Granulosa Cells, ABM Applied Biological Materials Inc., 1-3671 Viking Way, Richmond, BC, Canada V6V 2J5).
Heart cardio myoblasts line H9c2 were from ATCC.
MCF7 (epithelial cell line from female adenocarcinoma, has functional estrogen and EGF receptors and is dependent on estrogen and EGF for growth) from ATCC.
Fibroblasts from young female Alzheimer disease (AD) donor (AG07887) and older female patient (AG08629) were from Coriell Institute for Medical Research, Camden, N.J.
Lung cancer cell line A549 from ATCC.

In vitro MCF7 cells proliferation (E-SCREEN) assay: MCF-7 cells ($1 \times 10^3$ cells/well of a 96-well plate) were cultured with different micronutrients and plant extracts (0.5-5 µg/ml) with added β-17-estradiol (0.5 µg/ml) for 6 days at 37° C. Thereafter, medium in each well, including control wells, was replaced with 150 µl of tetrazolium MTT β-(4,5-dimethylthiazolyl-2)-2,5-diphenyltetrazolium bromide) (0.5 µg/ml in PBS). Wells that received DMSO only were used as negative control whereas that cells that receive only β-17-estradiol were use as positive control. Next, cells were incubated for 3 h at 37° C., the supernatant with MTT was removed, and the adherent cells were rinsed with PBS. Next, 150 µl of isopropanol was added to each well and the absorbance was measured at 570 nm using the microplate reader. Percentage of MTT reduction by metabolically active cell to purple formazan (reflecting cell proliferation rate) was calculated as following equation: Proliferation rate=$[(OD_{sample} - OD_{control})/OD_{control}]$.

FRAP (Ferric Reducing Antioxidant Power Assay) Sigma-Aldrich MAK369: Ferric reducing antioxidant power (FRAP) assay uses antioxidants as reductants in a redox-linked colorimetric reaction, wherein Fe3+ is reduced to Fe2+ at low pH which causes formation of a colored ferrous-probe complex. The antioxidant capacity of Basic Mix, Mix 1 and Mix 2, used at 500 and 100 µg/ml, was evaluated according to the manufacturer's protocol and change in absorption was measured at 594 nm. Antioxidant potential was expressed in mM Ferrous Equivalent (FE) Units and compared to positive control provided in the assay.

17 Beta Estradiol ELISA (Abcam ab108667): Immortalized Human Ovarian Granulosa Cells (HGL5) were grown in in PriCoat™-T75 Flasks, Prigrow IV medium supplemented with 10% FBS/5% Calf Serum/1% P/S. After 24 hrs the cells were trypsinized and plated into 96 well clear plate. Cells were allowed to attach for 24 hrs; then the seeding medium was removed and replaced by the same medium containing the test mixtures at concentrations 2, 1, and 0.5 μg/ml. Control included cells with the medium only and negative control contained cells exposed to 1 mM $H_2O_2$ as a damaging agent. After 24 hrs the treated cells were evaluated for β-17-estradiol production using in vitro competitive ELISA (Enzyme-Linked Immunosorbent Assay) kit.

A 96-well plate has been precoated with anti-estradiol IgG. Test samples (25 μl) and the Estradiol-HRP conjugate were added to the wells, where estradiol in the sample competes with the added estradiol-HRP for antibody binding. After 2 hour incubation at 37° C., the wells are washed to remove unbound material and TMB (3,3'5,5'-Tetramethylbenzidine) was used for the detection of Horseradish Peroxidase (HRP) activity. The reaction yields a blue color (Amax=652 nm) which changes to yellow (Amax=450 nm) upon the addition of either sulfuric or phosphoric acid which in the presence of HRP produces blue coloration. The reaction is terminated by addition of Stop Solution which results in a color change from blue to yellow. The intensity of signal is inversely proportional to the amount of Estradiol in the sample and the intensity is measured at 450 nm.

Progesterone synthesis ELISA (Thermo Fisher): Immortalized Human Ovarian Granulosa Cells (HGL5) were grown in in PriCoat™-T75 Flasks, Prigrow IV medium supplemented with 10% FBS/5% Calf Serum/1% P/S. After 24 hrs the cells were trypsinized and plated into 96 well clear plate. Cells were allowed to attach for 24 hrs; then the seeding medium was removed and replaced by the same medium containing the test mixtures (BM, Mix1 and Mix2) at 0.5 μg/ml. Control included cells with the medium only. After 24 hrs the treated cells were evaluated for Progesterone using in vitro competitive ELISA (Enzyme-Linked Immunosorbent Assay) kit (Thermo Fisher Scientific).

Specifically, a 96-well plate has been precoated with anti-Progesterone IgG. Test samples (5 mcl) and the Progesterone HRP conjugate were added to the wells, where progesterone in the sample competes with the added progesterone for antibody binding. After 2 hour incubation at room temperature, the wells were washed to remove unbound material and TMB (3,3'5,5'-Tetramethylbenzidine) was used for the detection of Horseradish Peroxidase (HRP) activity. The reaction yields a blue color (Amax=652 nm) which changes to yellow (Amax=450 nm) upon the addition of either sulfuric or phosphoric acid which in the presence of HRP produces blue coloration. The reaction was terminated by addition of Stop Solution resulting in a color change from blue to yellow. The intensity of signal inversely proportional to the amount of progesterone in the sample was measured at 450 nm. Detected amounts of progesterone were calculated from a standard curve and expressed in ng/ml.

ATP synthesis (Promega Corporation, CellTiter-Glo Luminescent Cell Viability Assay) 2800 Woods Hollow Rd-Madison, Wis. 53711, USA. The CellTiter-Glo® Luminescent Cell Viability Assay allows to determine the number of viable cells in culture based on quantitation of the ATP present, which signals the presence of metabolically active cells cultured in serum-supplemented medium. The homogeneous "add-mix-measure" format results in cell lysis and generation of a luminescent signal based on the luciferase reaction which is proportional to the amount of ATP present. The amount of ATP is directly proportional to the number of cells present in culture. The test cell line H9c2 (Heart cardio myoblasts) was grown in Dulbecco's modified Eagle's medium DMEM/10% FBS/1% PBS. After 24 hrs the cells were trypsinized and plated into 96 well white bottom plate. Cells were allowed to attach for 24 hrs; then the seeding medium was removed and replaced by the same medium without FBS containing the test mixtures (Basic Mix, Mix1 and Mix2) at concentrations of 2, 1, and 0.5 μg/ml, each. Control included cells with the medium only, negative control contained cells exposed to 1 mM $H_2O_2$. After 24 hrs the treated cells were subjected to Luminescent ATP detection Assay Kit according to the manufacturer's protocol.

ApoE and iNOS determination: Alzheimer disease (AD) fibroblasts from young female donor (AG07887), and older female patient (AG08629) and/or Normal Human fibroblasts (NHDF) and/or lung cancer cell line A549 were grown on DMEM/F12 without phenol red (Gibco, USA). Media was supplemented with charcoal stripped, sterile-filtered 10% fetal bovine serum (Sigma-Millipore, USA Origen), and 1% penicillin-streptomycin.

Cells were separated and splatted in 2 cm cell culture dishes and subjected to none or treated with IL-13 at 15 μg/ml, in the presence of Basic Mix (1 μg/ml), Mix1-1 (1 μg/ml), Mix1-2 (2 μg/ml), genistein (1 μg/ml), and estrogen E2 (5 nM) as indicated in each experiment. Treated cells were incubated for two hours or overnight followed by RNA isolation and purification for RT-PCR analysis.

Total RNA was obtained by standard method RNeasy* Plus, (Qiagen, Germany) lysing cells with RLT Plus buffer according to the manufacturer's instructions. Equal amount of RNA extracted from each treated lysate was reverse transcribed in 20 microliters reactions with RT-QuantiTech kit (Qiagen, Germany). 2 μl of the resulting cDNA containing specific primers of the gene of interest or reference gene, was amplified in 20 μl of SYBR-Green based master mix for qRT-PCR. Amplification in 40 cycles and Ct quantification was carried out in CFX-Connect PCR-system from BioRad. Relative expression of the target gene data was analyzed using delta Ct method and compared to delta Ct of expression of a reference gene. Specific primers for APOE, and a reference gene, Actin B, for gene expression analysis were obtained from Qiagen Gene Globe. iNOS2 was obtained from BioRAD. Each primer is verified by the manufacturer to ensure amplification of a single product and high PCR efficiency.

FIG. 1: Effects of micronutrient mixtures: Basic Mix, M1 and M2 on ATP synthesis in cardio myoblasts was studied. Heart myoblasts cells (H9c2) were grown in Dulbecco's modified Eagle's medium DMEM/10% FBS/1% PBS and processed as described in Material and Methods. For ATP determination, the cells were incubated in the same culture medium without FBS and test mixtures (Basic Mix, Mix1 and Mix2) were added each at concentrations of 2, 1, and 0.5 μg/ml. Control included cells with the medium only. After 24 hrs the treated cells were subjected to Luminescent ATP detection Assay Kit according to the manufacturer's protocol. Micronutrients are critical for production of biological energy (ATP) that is funneling the entire body metabolism, including DNA synthesis, oxygen transport, neuronal functions and other vital functions. Optimum energy supply is critical for brain and muscular function, it is important for cognitive and psychological processes, including mental and physical fatigue. There is also a tight interconnection between energy metabolism and fertility, above all in females. Vitamins, minerals and active plant components support mitochondrial function and ATP synthesis linking energy metabolism and fertility. In search for complex solutions to female related health aspects we evaluated the effects of nutrient combinations designated as: basic Mix, Mix 1 and Mix 2 on ATP synthesis in myocardial cells.

The results on FIG. 1 show that all test micronutrient mixtures were effective in increasing ATP synthesis in myocardial cells, compared to control. Basix Mix increased ATP production in these cells by 29% compared to Control. Highest efficacy in supporting cellular ATP synthesis was observed in the presence of Mix 1 and Mix 2 (451% and 439%, respectively compared to control.

Figure 2:
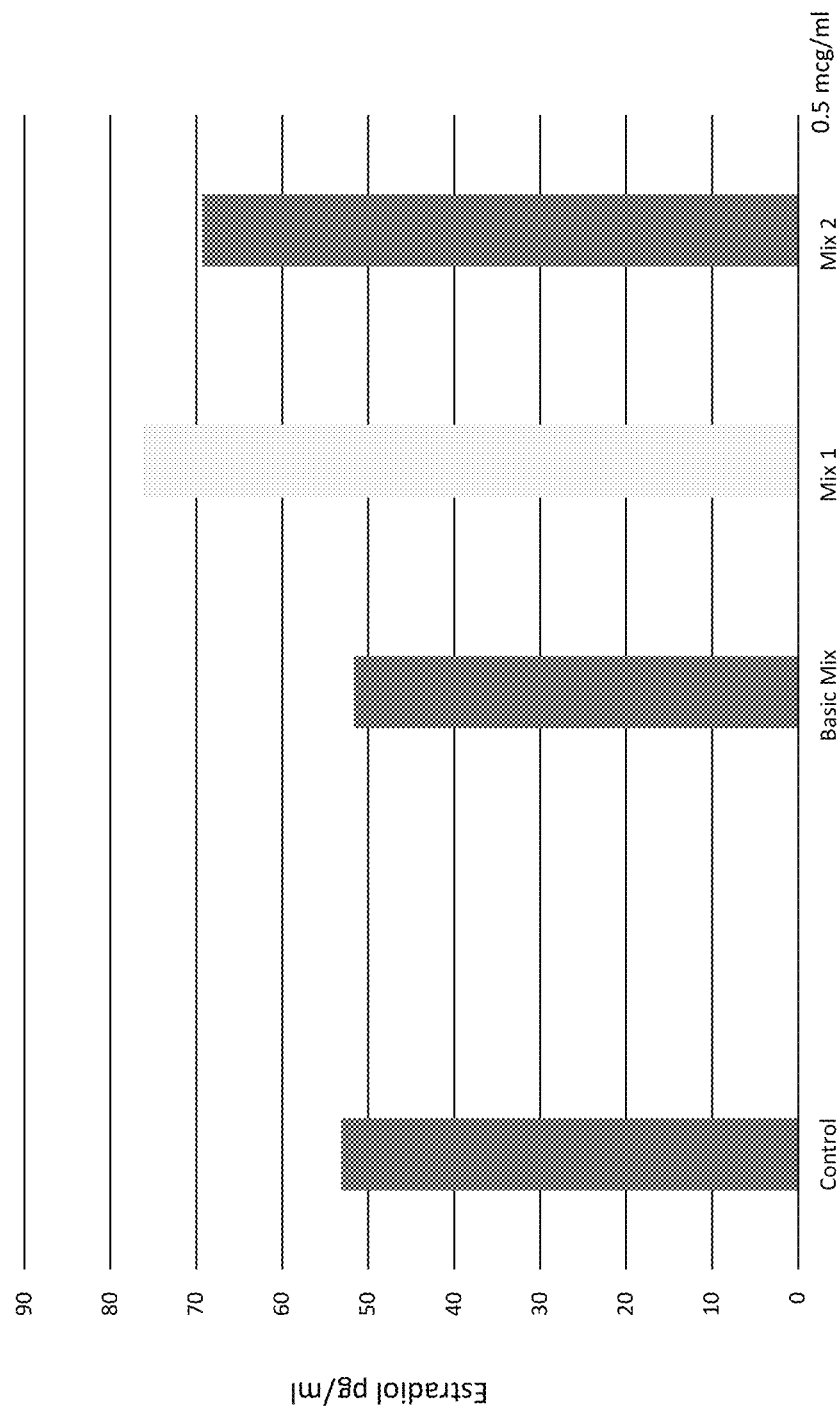
FIG. 2 shows effects of test micronutrient mixtures on 17 beta Estradiol synthesis in human ovarian granulosa cells is shown.

FIG. 2 shows effects of test micronutrient mixtures on 17 beta Estradiol synthesis in human ovarian granulosa cells is shown. Estrogen, a main female hormone, is responsible for developing and maintaining both the reproductive system and female characteristics. In addition, estrogen contributes to cognitive health, bone health, the function of the cardiovascular system, skin, mucous membranes and various essential bodily processes.

The most common risk factors for low estrogen levels include age (the ovaries produce less estrogen over time), family history of hormonal issues, such as ovarian cysts, or eating disorders. Decrease of estrogen during menopause is associated with various symptoms including hot flashes and night sweats, lower energy, mood changes, sleep problems, thinning hair, weight gain and a slower metabolism among other.

Estrogen replacement therapy (ERT) based on synthetic estrogen taken by many women to relieve pre- and menopausal symptoms has been associated with increased risk of breast cancer and other side effects. Important in protecting the endometrium (lining of the uterus), controlling overgrowth of cells of the endometrial lining and preventing endometriosis from forming helps to prevent overgrowth of certain types of cells, which can help protect against some cancers including those of the breast or the uterus maintaining HDL cholesterol levels (also known as the "good" cholesterol).

Beneficial in reducing symptoms associated with menopause, like mood swings, reducing adverse side effects of synthetic hormones, eases anxiety and promotes memory. Evaluation of the effects of basic Mix, Mix 1 or Mix 2 on estrogen and progesterone production by human ovarian granulosa cells is presented on FIG. 2 and FIG. 3.

Human Ovarian Granulosa Cells (HGL5) were grown for estrogen determination and 25 µl of each micronutrient mixture at concentrations 0.5 µg/ml and the estradiol-HRP conjugate were added to the wells, where estradiol in the sample competes with the added estradiol-HRP for antibody binding. After 2-hour incubation at 37° C., the wells were washed and TMB (3,3'5,5'-Tetramethylbenzidine) was added for the detection of Horseradish Peroxidase (HRP) activity and processed. Change in absorption at 450 nm was inversely proportional to the amount of estradiol in the sample. Control included cells with the medium.

Figure 3:
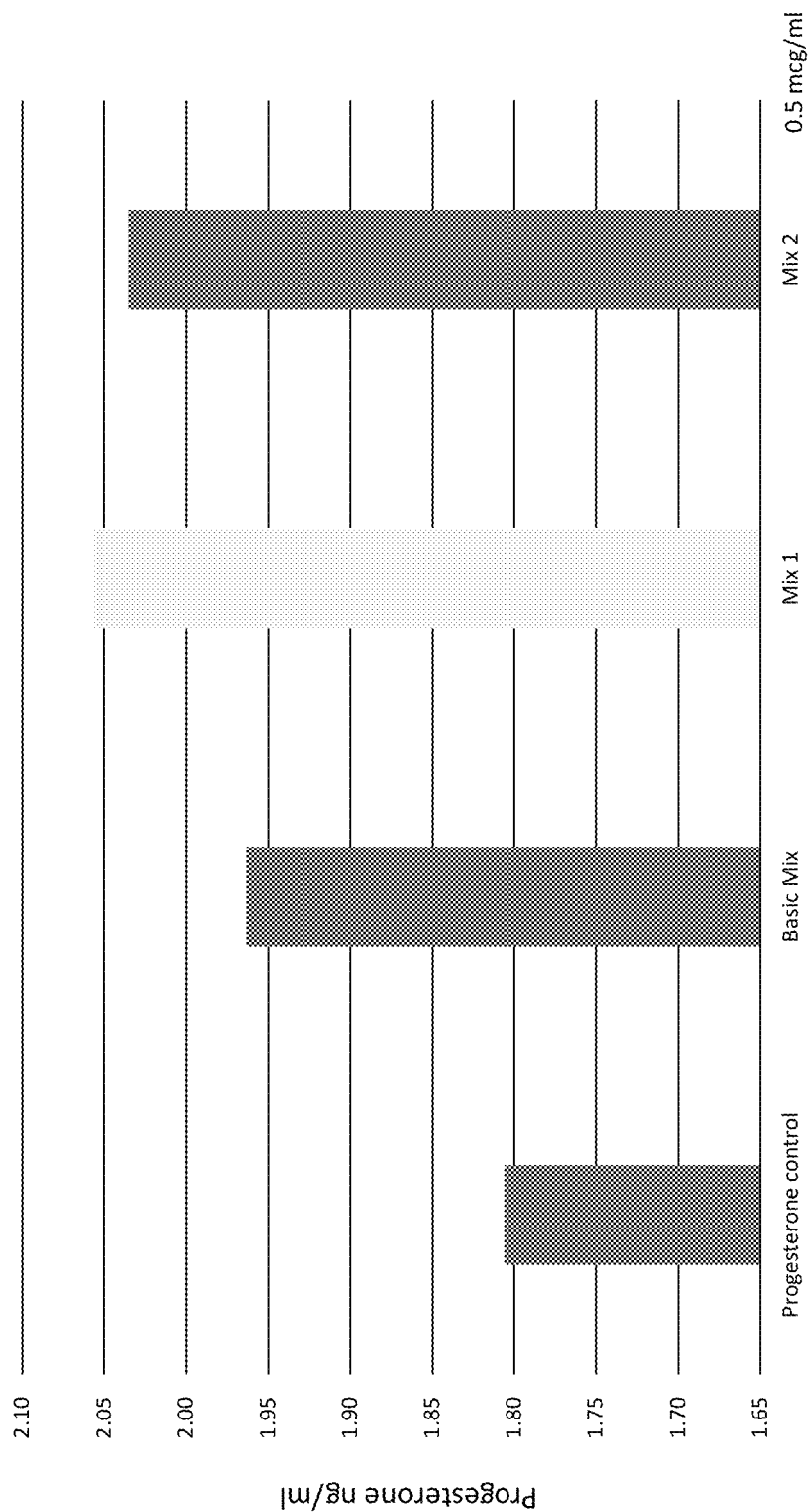
FIG. 3 shows effects of test micronutrient mixtures on progesterone synthesis in human ovarian granulosa cells.

FIG. 3 shows effects of test micronutrient mixtures (basic mix or Mix 1 or Mix 2) on progesterone synthesis in human ovarian granulosa cells. Human Ovarian Granulosa Cells (HGL5) were grown. The cells were incubated for 24 hr with 25 µl of test mixtures (basic mix, Mix 1 and Mix 2) at concentrations 0.5 µg/ml. Progesterone was detected using ELISA by change in absorption at 450 nm, which was inversely proportional to the amount of estradiol in the sample. Control included cells with the medium. The results on FIG. 2 and FIG. 3 show that human ovarian granulosa cells exposed to Mix 1 and Mix 2 have higher cellular synthesis of 17 beta Estradiol and progesterone compared to basic mix and controls. All test mixtures were applied at 0.5 mcg/ml.

The highest increase in estradiol production (by 43%) and progesterone by 13% was observed in the presence of Mix 1 compared to control. In the presence of Mix 2 the cellular production of estradiol was higher by 30% and progesterone by 13%. Basic mix applied at 0.5 mcg/ml concentration had no or minimal stimulatory effect on estradiol and progesterone secretion by human ovarian granulosa cells compared to control.

Figure 4:
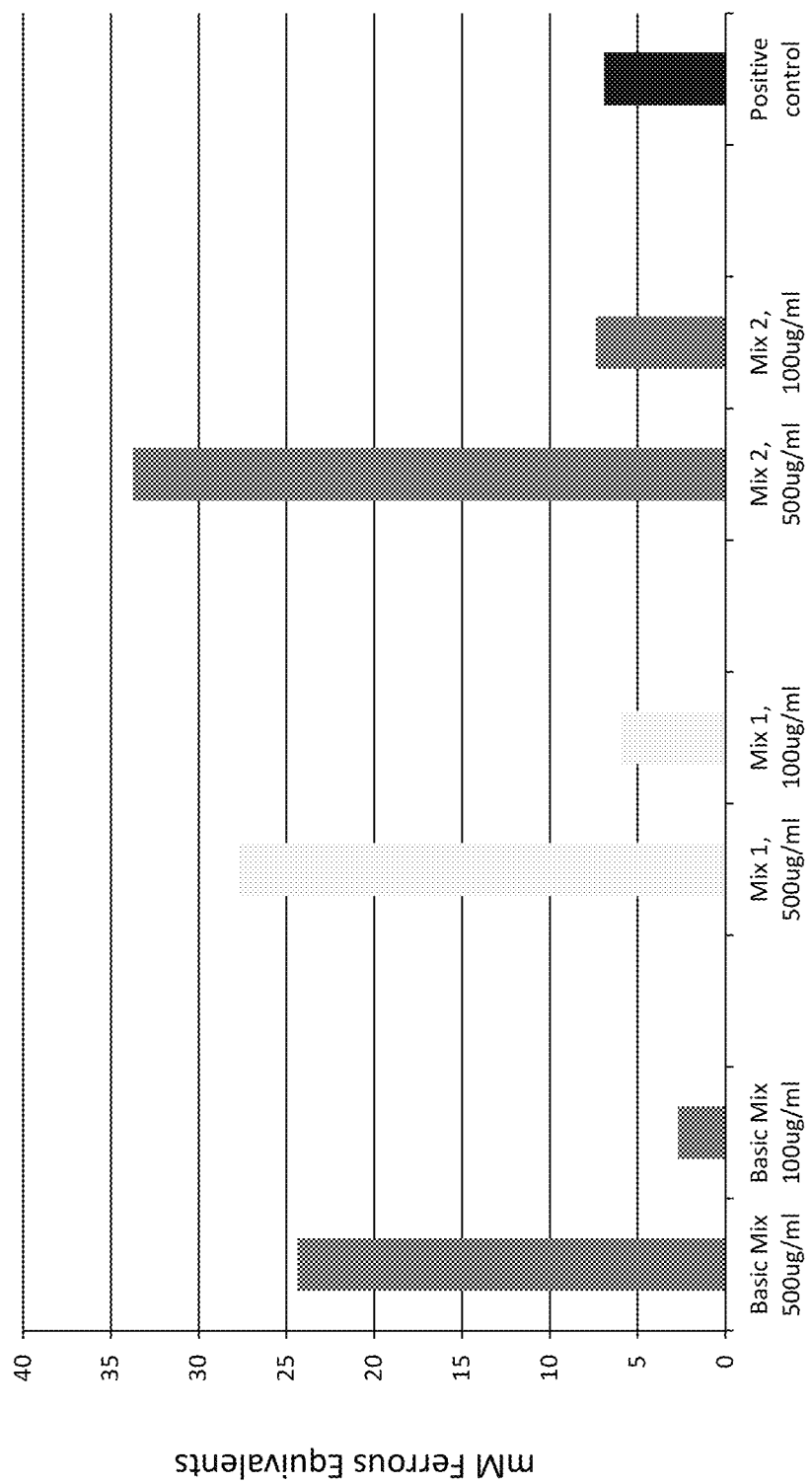
FIG. 4 shows antioxidant potential of test micronutrient mixtures (FRAP assay).

FIG. 4 shows antioxidant potential of test micronutrient mixtures (FRAP assay). Oxidative stress is highly pathogenic and associated with numerous diseases, including female reproductive diseases and impairing fertility. Oxidative damage can affect variety of physiological mechanisms such as oocyte maturation, fertilization, implantation, embryo development and hence contributes to the pathophysiology of pregnancy related complications, endometriosis, polycystic ovarian disease, unexplained infertility and gynecological cancers.

Various antioxidant vitamins and supplements have been recommended to balance pro-oxidant and anti-oxidant cellular processes, but efficacy of their combinations is rarely evaluated.

We used FRAP assay (ferric reducing ability of plasma) that has been applied to measure antioxidant capacity of food and antioxidant potential of various micronutrient mixtures. The assay is based on the reduction of ferric-tripyridyltriazine ($Fe^{3+}$-TPTZ) to an intense blue color ferrous-tripyridyltriazine complex ($Fe^{2+}$-TPTZ) with an absorption maximum at 593 nm. In this assay, trolox is mostly used as positive control, and results are expressed as mM ferrous equivalents calculated from a standard curve.

The antioxidant capacity of basic mix, Mix 1 and Mix 2, used at 500 and 100 µg/ml, was evaluated according to the manufacturer's protocol and change in absorption was measured at 594 nm. Antioxidant potential was expressed in mM Ferrous Equivalent (FE) Units and compared to positive control provided in the assay. The FIG. 4 shows that all test nutrient combinations had concentration dependent and significantly high antioxidant capacity compared to control.

The highest antioxidant potential among test combinations was observed with Mix 2 at 500 mg/ml with 489% increase in FE equivalents compared to control. At the same 500 mg/ml concentrations the Mix 1 had 400% higher antioxidant capacity compared to control, and the basic Mix showed 353% higher antioxidant potential compared to control.

Figure 5:
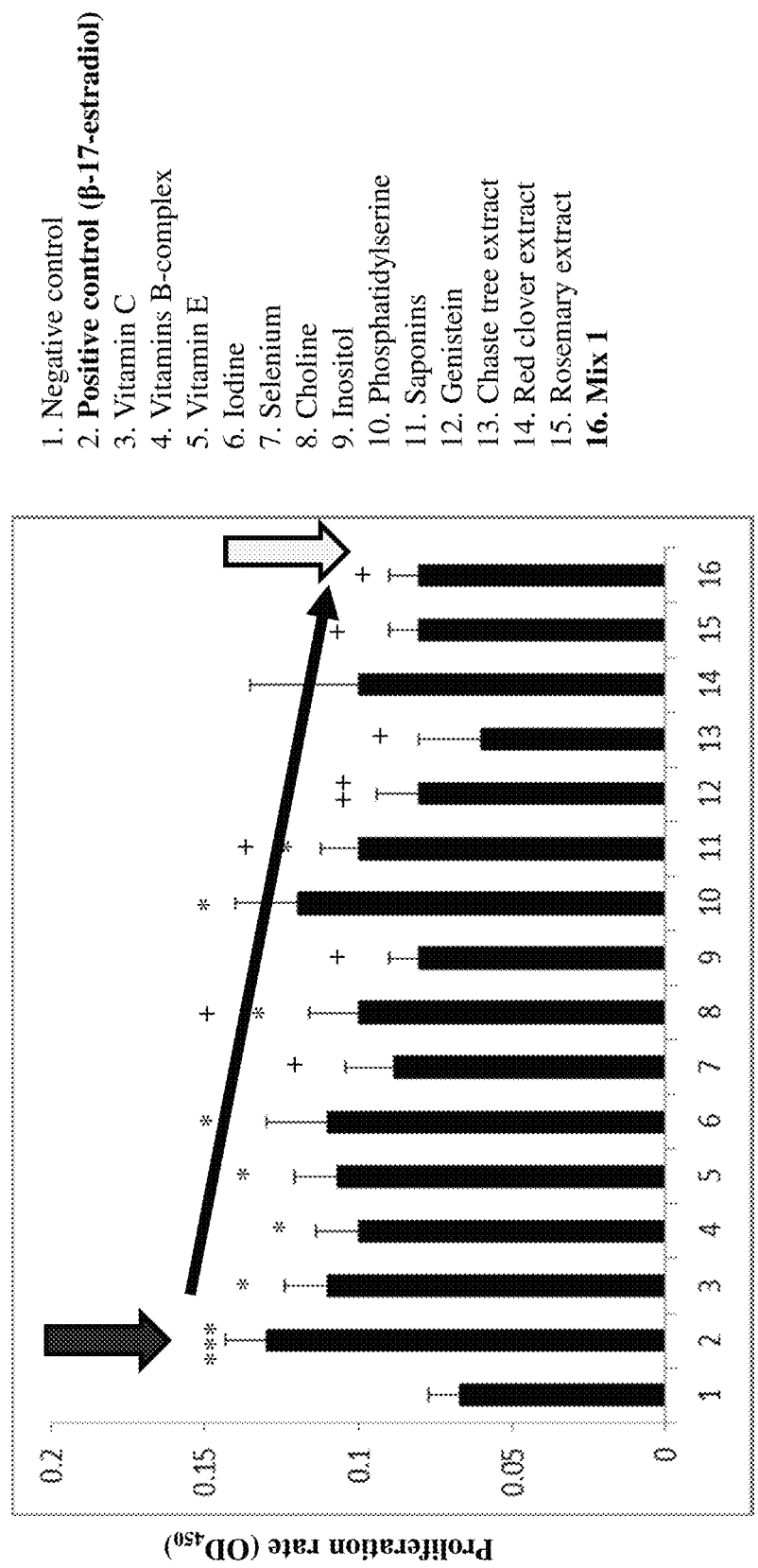
FIG. 5 shows effects of individual compounds and their combination on proliferation of estrogen-dependent breast cancer cells.

FIG. 5 shows effects of individual compounds and their combination on proliferation of estrogen-dependent breast cancer cells. Efficacy of all three test mixes against breast cancer was tested, specifically proliferation of estrogen-dependent breast cancer cells in females. Breast cancer is the most common cancer in women in the USA. It occurs in every country of the world in women at any age after puberty but with increasing rates in later life. About 70-80% of breast cancers are hormone-receptor positive.

We used MCF7 cancer cells which are epithelial cells isolated from the breast tissue of a female patient with metastatic adenocarcinoma and depend on estrogen to proliferate. These cells are commonly used for in vitro studies because they retained several characteristics particular to mammary epithelium, such as the processing of estrogen, in the form of estradiol, via estrogen receptors in the cell cytoplasm. We tested the effects of individual natural compounds and their combination (Mix 1) on proliferation rate of human MCF7 cells in the presence of beta-17 estradiol, the primary female sex hormone.

In vitro E-SCREEN assay on tetrazolium (MTT) reduction test of MCF-7 cell line treated with different micronutrients and plant extracts (0.5 µg/ml) in the presence of β-17-estradiol (0.5 µg/ml) for 6 days at 37° C. as described in Materials and Methods. Values shown are mean±standard deviation (n=4). Value significantly different from corresponding negative control at * p<0.05,  p<0.01, * p<0.001; +p<0.05, ++p<0.01 compared to positive control. The results in FIG. 5 show that human MCF7 cells exposed to beta-17 estradiol, the primary female sex hormone, had higher proliferation rate by about 1.2 folds compared to normal control. In the presence of beta-17 estradiol all individual compounds decreased cancer cells proliferation but at a different degree. The combination of micronutrients in Mix 1 was effective in lowering MCF-7 cells proliferation by about 40% compared to beta-17 estradiol control. This difference was statistically significant.

Figure 6:
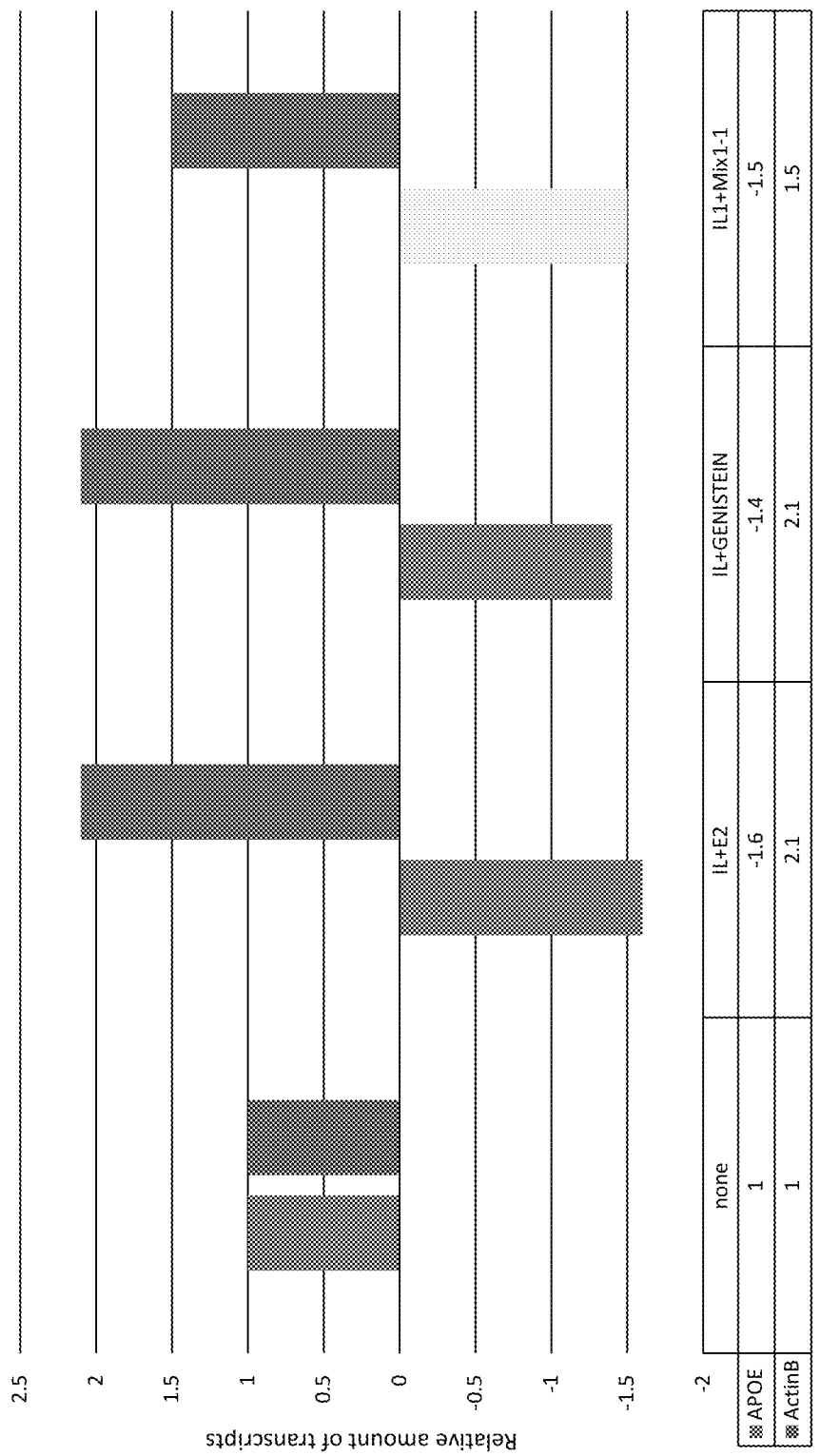
FIG. 6 shows transcriptional repression of ApoE gene in lung cancer cells by basic mix, Mix 1, and genistein in the presence of IL1β.

FIG. 6 shows transcriptional repression of APOE gene in lung cancer cells by basic mix, Mix 1, and genistein in the presence of IL10. Human non-small lung cancer cell line A549 was maintained in cell culture and processed for RNA extraction and RT-PCR as described in Materials and Methods. The results show the relative amounts of transcripts of APOE gene of non-treated cells (control), and cells exposed to Mix 1 at 4 µg/ml, estrogen at 5 nM, and genistein 1 ug/ml in the presence of IL-1 at 15 µg/ml all final concentration in culture media, as indicated, compared to the amount of transcripts for the reference gene (β-actin).

According to the American Lung Association, over the past 42 years the diagnoses of lung cancer in women increased 84% while dropping 36% among men over the same period. Approximately 20% of women diagnosed with lung cancer today are lifelong non-smokers (by contrast only 1 in 12 men with lung cancer never smoked). Lung cancer in women has exceeded both the incidence and mortality for breast cancer. It became the leading cause of cancer death in developed countries such as the United States and some from Europe In order to mimic cancer microenvironment, we exposed human lung cancer cells to pro-inflammatory cytokine IL1b which has critical function in malignancies, influencing the tumor microenvironment and promoting cancer initiation and progression.

We used RT-PCR technology to evaluate the effects of Mix 1 on cellular expression of important markers associated with cancer—ApoE and iNOS. The effects of Mix 1 were compared to the effects of estrogen and genistein (natural estrogenic compound) which are included in all test mixes.

ApoE and iNOS and their significance in cancer: ApoE gene provides instruction for making a protein called Apolipoprotein (ApoE). It is a multifunctional protein which plays important roles in our metabolism as it binds to and transports cholesterol and fatty molecules, and its high expression has been linked to development of neurodegenerative diseases, cardiovascular disease and cancer.

ApoE is also known to induce inflammation in the tumor microenvironment as its overexpression promotes cancer growth and migration and contributes to an aggressive clinical course in patients with lung cancer. On the other hand iNOS (inducible NO synthase) is required to produce nitric oxide (NO) which is involved in multiple physiological functions, including cardiovascular, immune and neurological functions and plays a role both in health and various pathologies.

iNOS has been expressed significantly higher in numerous tumors, including breast, ovarian, lungs and many other. Its higher expression has been associated with higher tumor vascularization, and other cancer promoting processes. The results in FIG. 6 show that Mix 1 was effective in decreasing ApoE transcripts in human lung cancer under pro-inflammatory condition (in the presence of cytokine, IL1b).

This beneficial inhibitory effect of Mix 1 on ApoE was similar to the effects of estrogen and genistein (plant estrogenic compound). Actin B (ACTB) served as independent control The application of Mix 1 represents superior health benefits over genistein or estrogen alone by its simultaneous additional effects on other anti-cancer cellular mechanisms which can lead to pleiotropic control of the malignancy process. Moreover, significant efficacy of the Mix 1 in lowering ApoE expression could be achieved through its other constituents as the Mix 1 contains much smaller concentration of genistein than used individually in this test.

Figure 7:
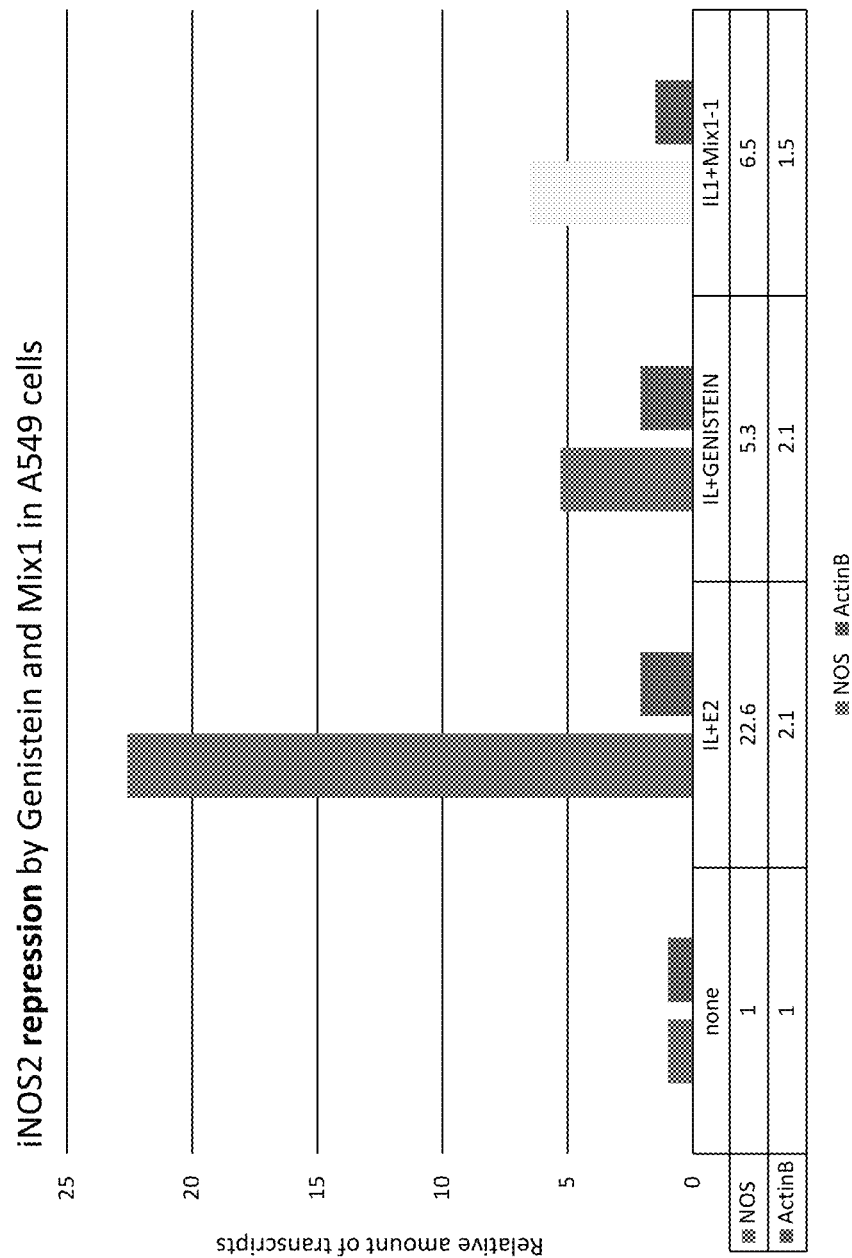
FIG. 7 shows changes in iNOS expression in lung cancer cells exposed to Mix1, estrogen, and genistein under pro-inflammatory conditions (in the presence of IL-1β).

FIG. 7 shows changes in iNOS expression in lung cancer cells exposed to Mix 1, estrogen, and genistein under pro-inflammatory conditions (in the presence of IL-1β). Human non-small lung cancer cell line A549 was maintained in cell culture and processed for RNA extraction and RT-PCR. The results show the relative amounts of transcripts of iNOS gene of non-treated cells (control), and cells exposed to Mix1 at 4 µg/ml, estrogen 5 nM and genistein 1 mcg/ml in the presence of IL-1 at 15 µg/ml as indicated, compared to the reference gene (Actin B). Evaluation of the effects of Mix 1 on lung cancer cells were done on mammalian cells. In order to mimic cancer microenvironment, human lung cancer cells were exposed to pro-inflammatory factor—cytokine IL1b—which has critical function in malignancies by promoting cancer initiation and progression. Untreated cancer cells served as control.

Under this condition, the anti-cancer effects of Mix 1 and estrogenic compounds present in the mix were evaluated by RT-PCR technique by measuring the amount of synthesized mRNA for two important proteins used as markers of cancer: ApoE and iNOS.

Figure 8:
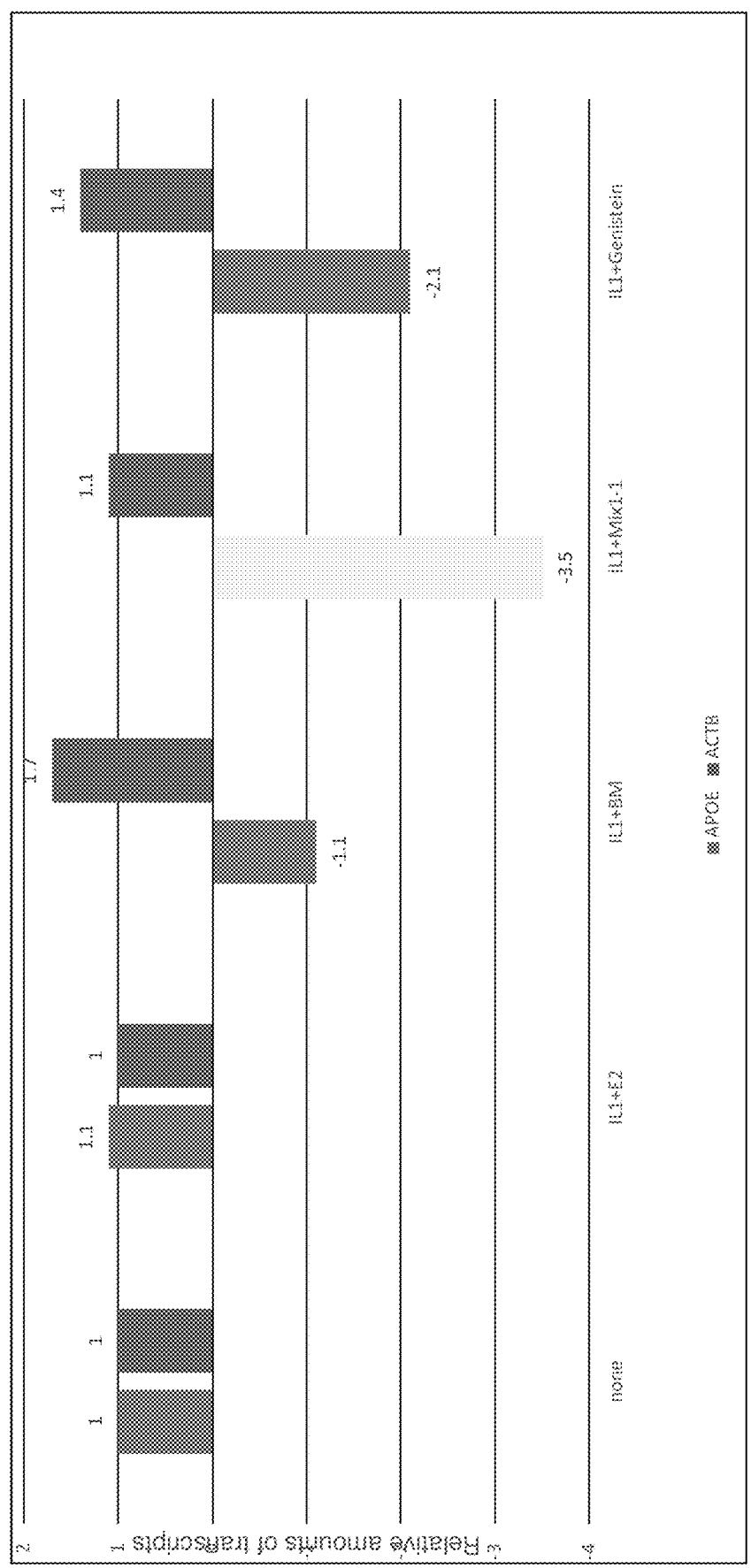
FIG. 8 shows transcriptional repression of ApoE gene in fibroblasts cells (old Alzheimer's disease donor) by Mix 1, basic mix, and estrogen in the presence of IL-1β.

The results in FIG. 7 show that under pro-inflammatory conditions (presence of Il1b) estrogen increased expression of iNOS in human lung cancer cells more than 20 times over control. Mix 1 (1 mcg/ml) significantly reduced iNOS expression under this pro-inflammatory conditions by lowering iNOS transcript by more than 4 times. This inhibitory effect was comparable to genistein at 1 mcg/ml. The efficacy of Mix 1 can be superior to genistein alone as significant inhibitory effect on iNOS could be achieved with much smaller amount of genistein combined in the Mix1. Presence of other micronutrients in Mix1 expands to other cellular mechanisms important for overall anti-cancer effects. The efficacy of Mix 1 in decreasing breast cancer cells proliferation and cellular production of two important lung cancer markers by acting at the genetic level indicate that micronutrients in Mix 1 has broader anti-cancer effects. Since ApoE and iNOS2 are elevated also in other cancers, the benefits of Mix1 may expand to various types of cancers FIG. 8 shows transcriptional repression of ApoE gene in fibroblasts cells (old Alzheimer's disease donor) by Mix 1, basic mix, and estrogen in the presence of IL-1β. Alzheimer disease (AD) fibroblasts (AG08629) were maintained and processed for RT-PCR determination as described in Materials and Methods. The figure shows the relative amounts of transcripts of ApoE gene and reference Actin B gene in fibroblasts cells (old female AD donor) non-treated and exposed to IL10 together with estradiol (5 nM), basic mix (4 ug/ml) and Mix 1 (4 g/ml). ApoE has a paramount role in lipid metabolism by regulating transport and metabolism of cholesterol, triglycerides and phospholipids in multiple tissues. However, increased ApoE levels and female gender are considered risk factors for cognitive decline and Alzheimer's disease.

ApoE gene is responsible for the production of protein present in the central nervous system and the periphery, which represents a critical link between these two compartments and could influence Alzheimer's disease pathogenesis by disrupting the blood-brain barrier integrity from both sides. ApoE can also impact peripheral immunity and inflammation. Various data demonstrate that in response to a peripheral inflammatory stimulus, a pro-inflammatory cytokine production is higher with ApoE4. We used RT-PCR technique to evaluate efficacy of test Mix 1 and Basic Mix (BM) on decreasing ApoE expression in the presence of pro-inflammatory conditions (Il1b) in comparison to the individual effects of estrogen and a plant estrogenic compound-genistein.

Results in FIG. 8 show that Mix 1 at 1 mcg/ml concentration applied to cells derived from young AD donor and tested under pro-inflammatory conditions (Il1b) was the most effective compared to basic mix and estrogen in decreasing ApoE. In the presence of Mix 1 at 1 mcg/ml ApoE transcription decreased by 3.5, while in the presence of Basic Mix a decrease was 1.1 times. Estrogen had positive effects equal to control on ApoE expression. Actin B (ACTB) served as independent control for gene transcription.

Figure 9:
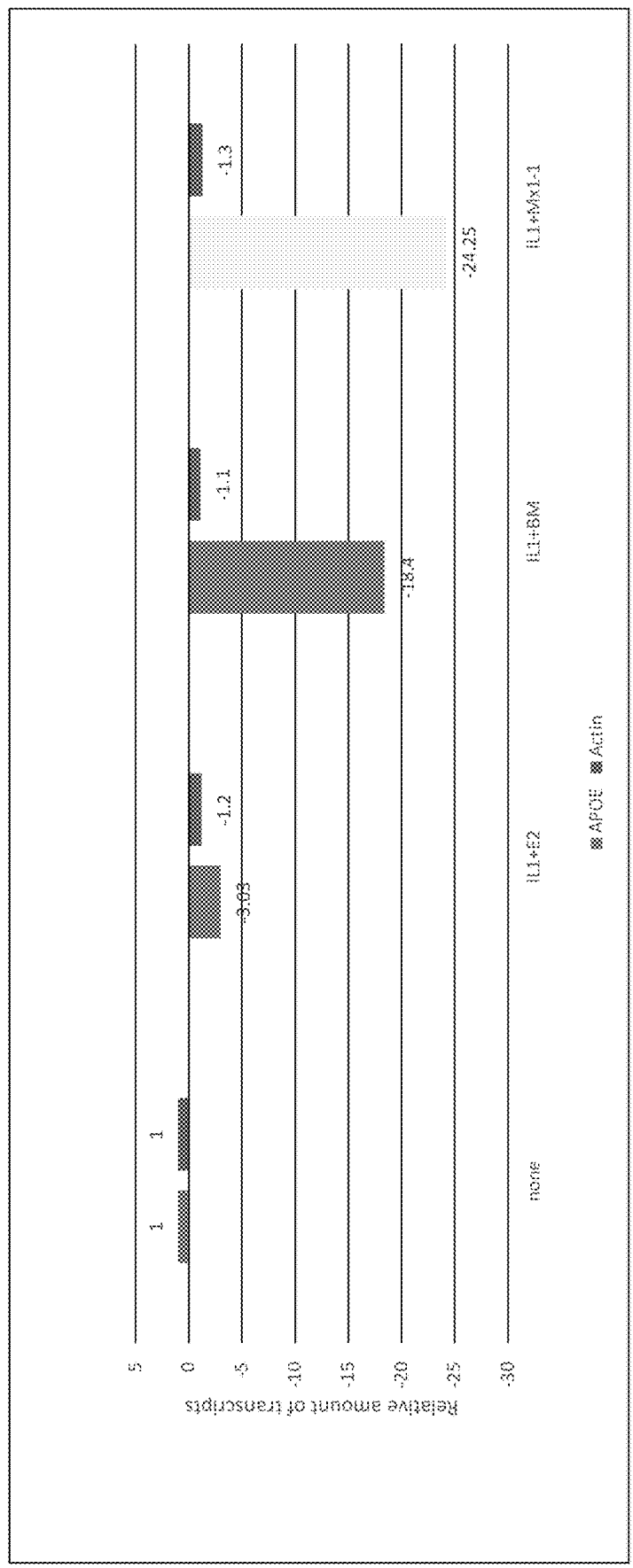
FIG. 9 shows transcriptional repression of ApoE gene in fibroblasts cells (old Alzheimer's disease donor) by Mix 1, basic mix and estrogen in the presence of IL-1β.

FIG. 9 shows transcriptional repression of ApoE gene in fibroblasts cells (old Alzheimer's disease donor) by Mix 1, basic mix and estrogen in the presence of IL-1β. Alzheimer disease (AD) fibroblasts from old female patient (AG08629) were maintained and processed for RT-PCR determination as described in Materials and Methods. The figure shows the relative amounts of transcripts of ApoE gene and reference Actin B gene in fibroblasts cells (young female AD donor) induced with IL10β, and non-treated or treated with 5 nM estradiol (5 nM), Basic Mix (BM) (1 ug/ml), and Mix1-1 (4 µg/ml). Results in FIG. 9 shows that Mix 1 at 1 mcg/ml concentration and under pro-inflammatory conditions (Il1b) was the most effective compared to basic mix and estrogen in decreasing ApoE transcript in fibroblast cells derived from old Alzheimer's female patient. In the presence of Mix 1 at 1 mcg/ml ApoE transcription decreased by over 24 times. Cell exposure to Basic Mix resulted in ApoE transcript decrease by about 18 times and in the presence of estrogen there was about 3 times ApoE decrease compared to "no treatment" control. Actin B (ACTB) served as independent control for gene transcription.

Figure 10:
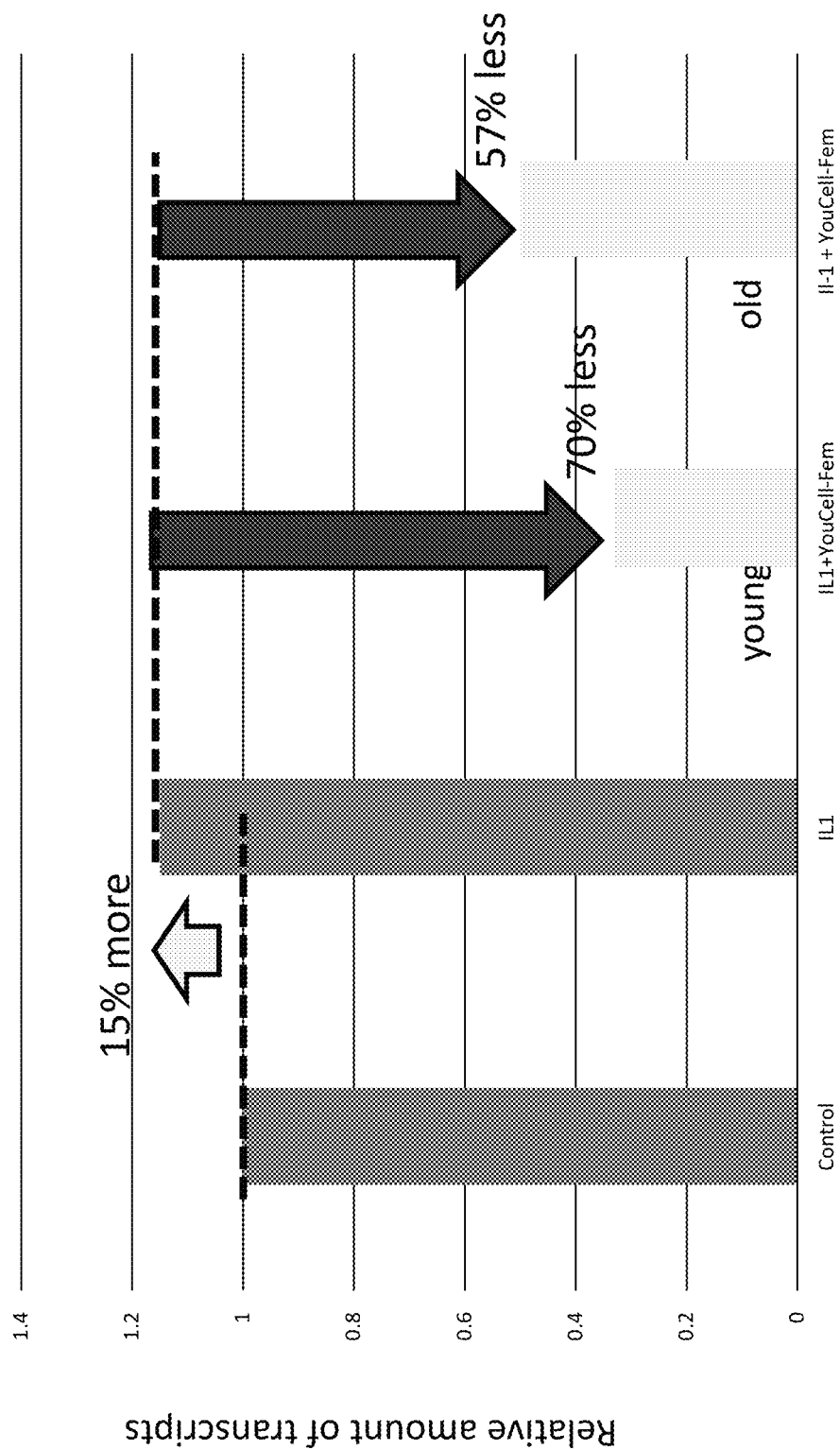
FIG. 10 shows Mix 1 inhibits transcription of ApoE gene in fibroblasts from young and old Alzheimer's disease patients under pro-inflammatory conditions.

FIG. 10 shows Mix 1 inhibits transcription of ApoE gene in fibroblasts from young and old Alzheimer's disease patients under pro-inflammatory conditions. Alzheimer disease (AD) fibroblasts from young (AG07887) and old (AG08629) female AD patient and were maintained and processed for RT-PCR determination as described in materials and methods section. The figure shows changes in relative amounts of ApoE transcripts in fibroblasts from young and old female donor in the presence of IL1β and compared to non-treated control. Results in FIG. 10 shows that under pro-inflammatory condition (with IL1b) Mix 1 was effective in decreasing ApoE transcript by 70% in cells derived from young AD donor and by 57% in cells old AD donor cells.

Figure 11:
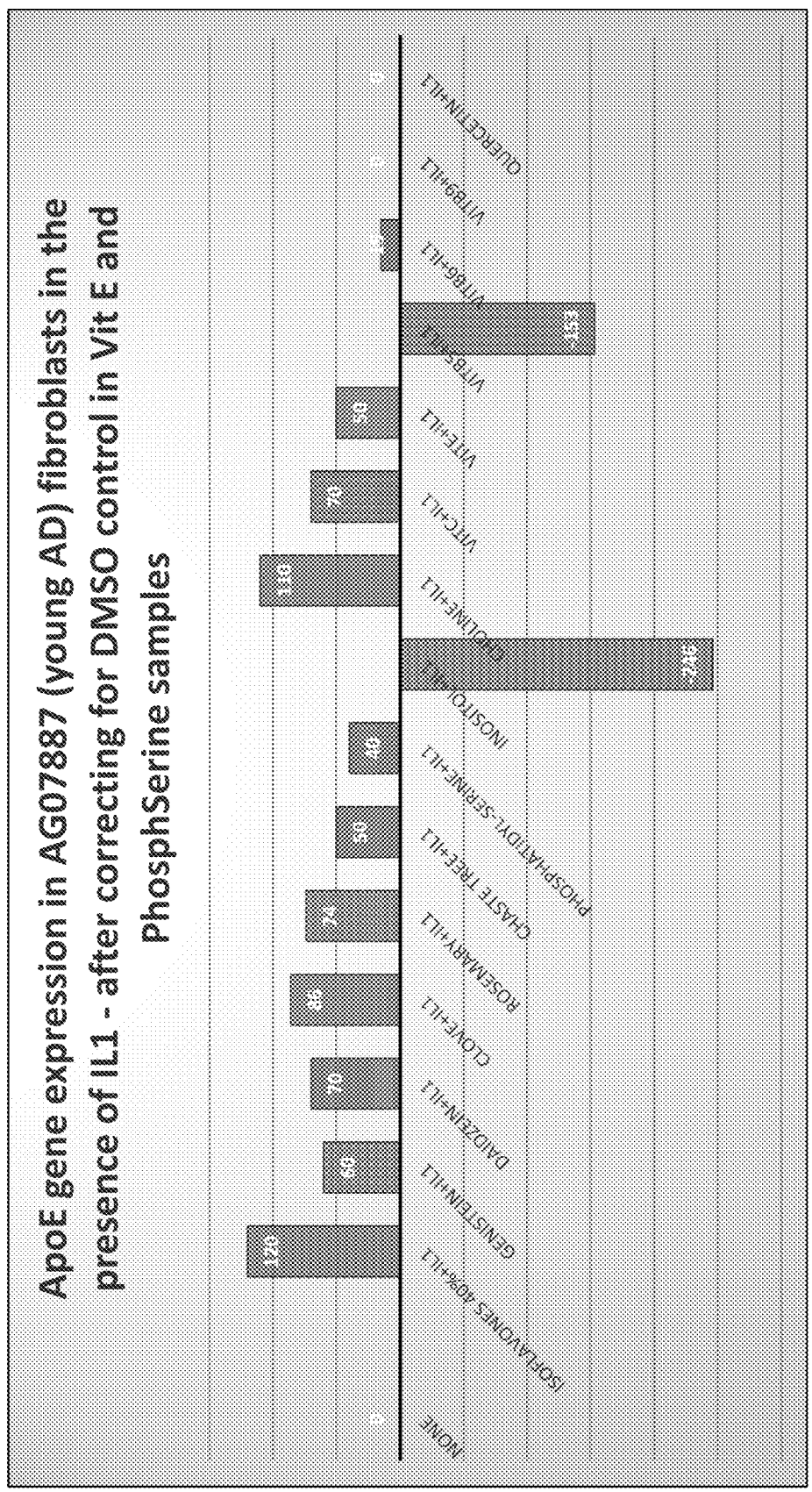
FIG. 11 shows effects of individual components on transcription of ApoE gene under pro-inflammatory conditions in fibroblasts derived from young female Alzheimer's disease patient.

FIG. 11 shows effects of individual components on transcription of ApoEgene under pro-inflammatory conditions in fibroblasts derived from young female Alzheimer's disease patient. Alzheimer disease (AD) fibroblasts from young (AG07887) female AD patient and were maintained and processed for RT-PCR determination as described in Materials and Methods. Cells were incubated overnight with no addition or 15 µg/ml IL1b and/or with individual compounds dissolved in phosphate buffered saline (PBS) and applied at final concentrations of 1 ug/ml. Vitamin E, phosphatidyl serine, and inositol were dissolved in DMSO to a final concentration of 0.1% in the cell culture media. Changes in ApoE mRNA expression for these components were corrected for the presence of DMSO. After treatment the cells lysates were subjected to RNA isolation, reverse transcribed and the ApoE gene was amplified and quantified by RT-PCR. The graph shows the relative number of transcripts of ApoE gene (%) compared to ApoE transcripts in non-treated cells. Each value was standardized to the number of transcripts of Actin B as housekeeping reference gene.

Figure 12:
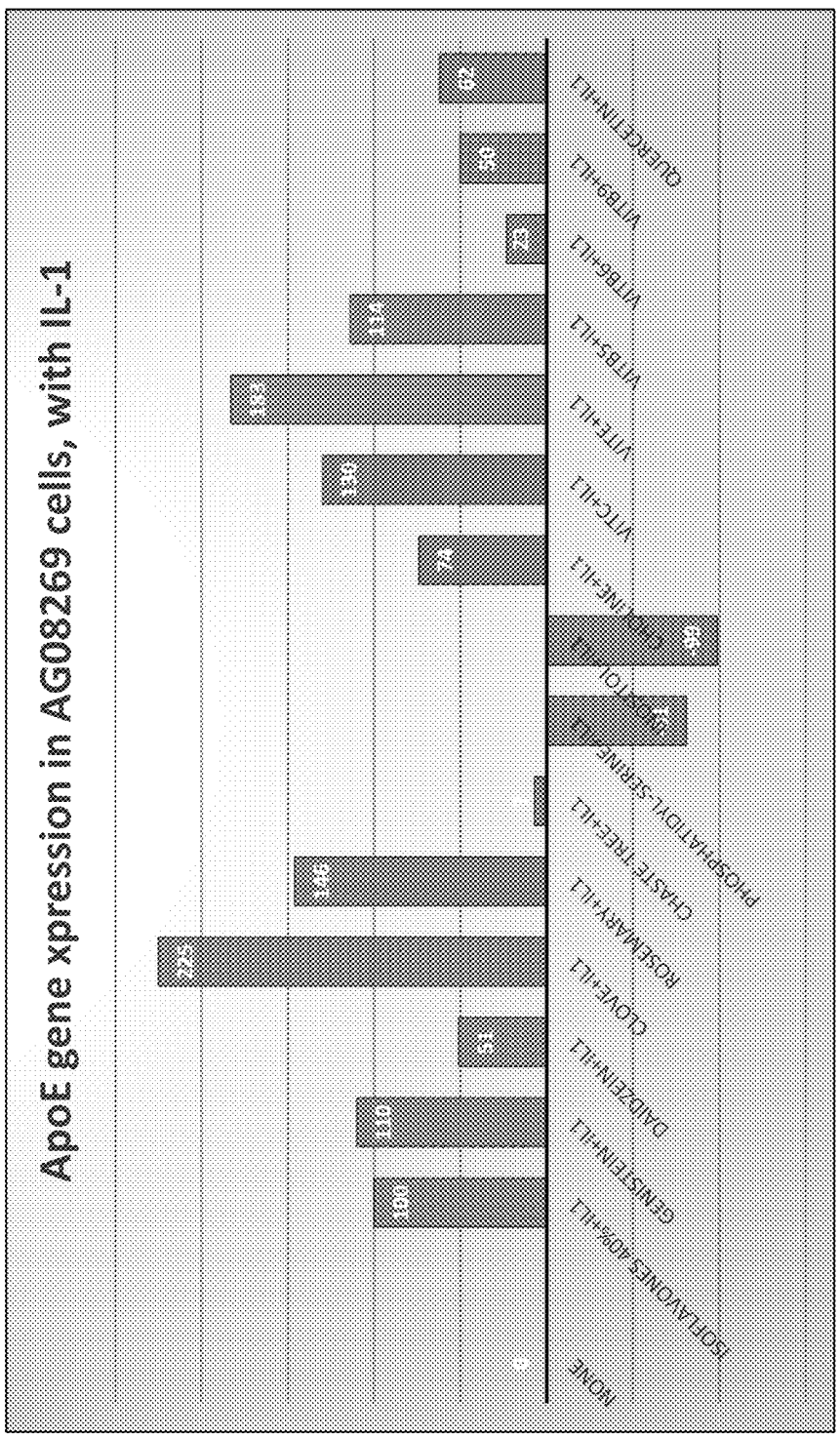
FIG. 12 shows effects of individual components on transcription of ApoE gene in fibroblasts under pro-inflammatory conditions from old female Alzheimer's disease patients.

FIG. 12 shows effects of individual components on transcription of ApoE gene in fibroblasts under pro-inflammatory conditions from old female Alzheimer's disease patients. Effects of individual components on transcription of ApoE gene under pro-inflammatory conditions in fibroblasts derived from old female Alzheimer's disease patient: Alzheimer disease (AD) fibroblasts were treated or not with IL1b alone and/or with the individual compounds as indicated. Final concentrations for individual compounds were at 1 ug/ml. Vitamin E, phosphatidyl serine, and inositol were dissolved in DMSO to a final concentration of 0.1% in the cell culture media. Changes in ApoE mRNA expression for these components were corrected for DMSO solvent. After treatment the cells lysates were subjected to RNA isolation, reverse transcribed and the ApoE gene was amplified and quantified by RT-PCR. The graph shows the relative number of transcripts of ApoE gene (%) compared to ApoE transcripts in non-treated cells. Each value was standardized to the number of transcripts of Actin B as housekeeping reference gene.

Figure 13:
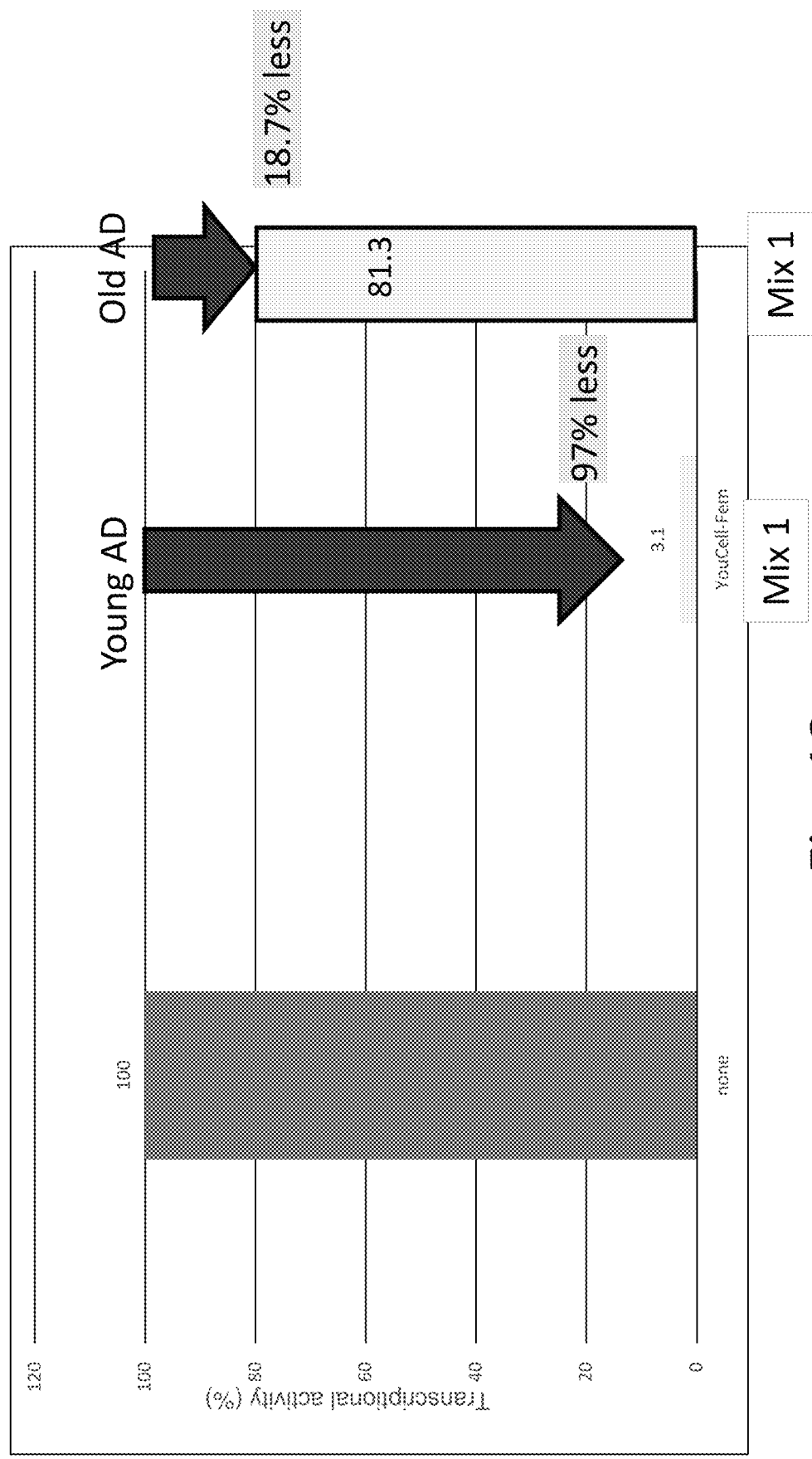
FIG. 13 shows Mix 1 inhibits ApoE gene transcription in fibroblasts cells from young and old female Alzheimer's disease donors under normal conditions (without IL1β).

FIG. 13 shows Mix 1 inhibits ApoE gene transcription in fibroblasts cells from young and old female Alzheimer's disease donors under normal conditions (without IL1β). Alzheimer disease (AD) fibroblasts from old and young female patient were grown in DMEM culture media and were treated with no addition and 4 ug of Mix1 as indicated. After overnight treatment the cells lysates were subjected to RNA isolation, reverse transcribed and the ApoE gene was amplified and quantified by RT-PCR. The graph shows the relative number of transcripts of ApoE gene (%) compared to ApoE transcripts in non-treated cells. Each value was standardized to the number of transcripts of Actin B as housekeeping reference gene. Results in FIG. 13 show that under normal conditions (without IL1b) Mix 1 was effective in decreasing ApoE transcript by 97% in cells derived from young AD donor and by 18.7% in cells old AD donor cells.

Figure 14:
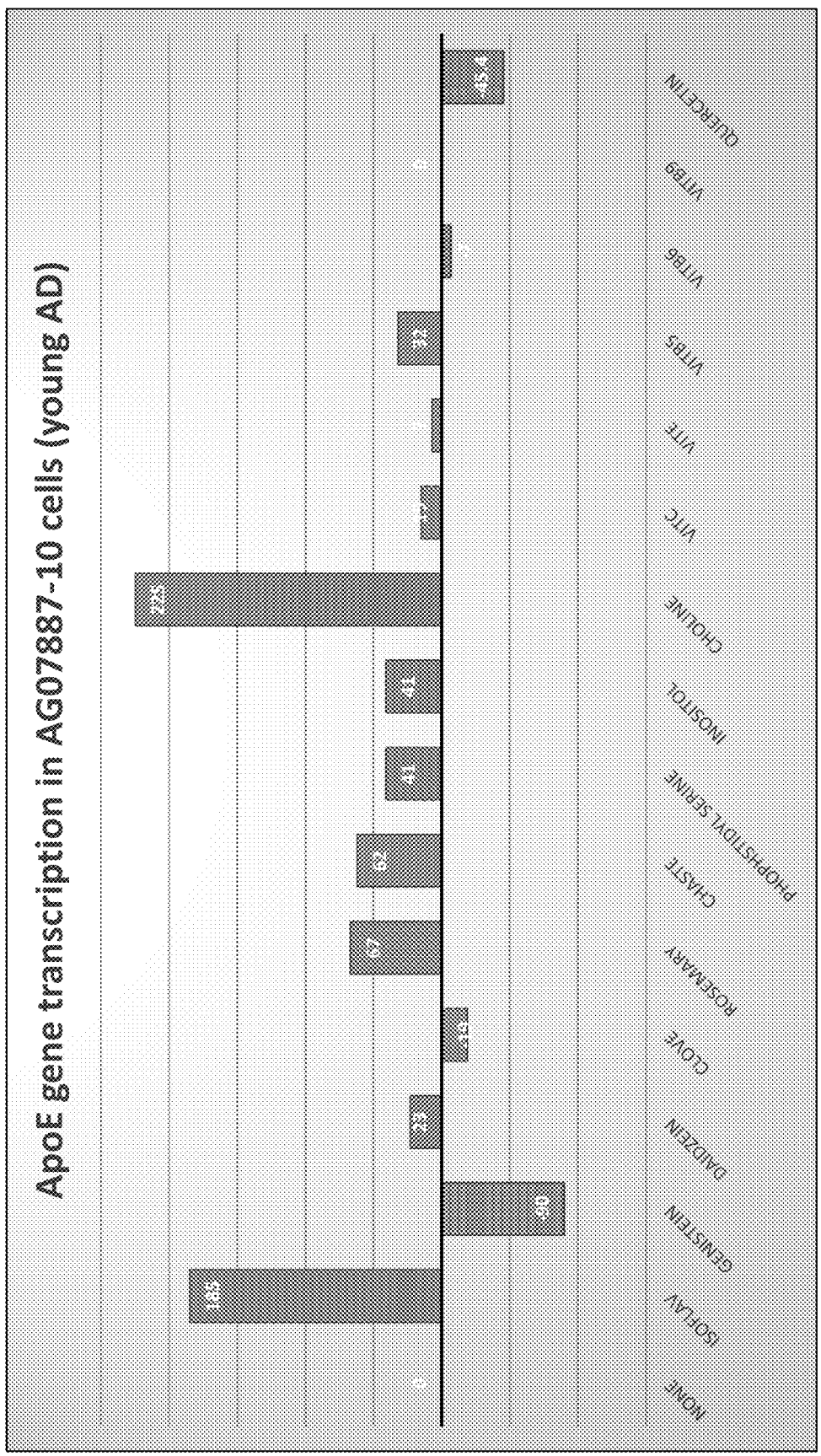
FIG. 14 shows effects of individual components on ApoE gene transcription in fibroblasts cells from young Alzheimer's disease female donor under normal conditions (without IL1β).

FIG. 14 shows effects of individual components on ApoE gene transcription in fibroblasts cells from young Alzheimer's disease female donor under normal conditions (without IL1). Alzheimer disease (AD) fibroblasts from young female AD patient were grown in DMEM as described in Materials and Methods, afterwards they were non-treated or treated with the individual compounds as indicated. Final concentrations for individual compounds were at 1 ug/ml. Vitamin E, phosphatidyl serine, and inositol were dissolved in DMSO with its final concentration of 0.1% in the cell culture media. Changes in ApoE mRNA expression for these components were corrected for DMSO solvent. After overnight treatment with individual ingredients the cells lysates were subjected to RNA isolation, reverse transcribed and the ApoE gene was amplified and quantified by RT-PCR. The graph shows the relative number of transcripts of ApoE gene (%) compared to ApoE transcripts in non-treated cells. Each value was standardized to the number of transcripts of Actin B as housekeeping reference gene.

Figure 15:
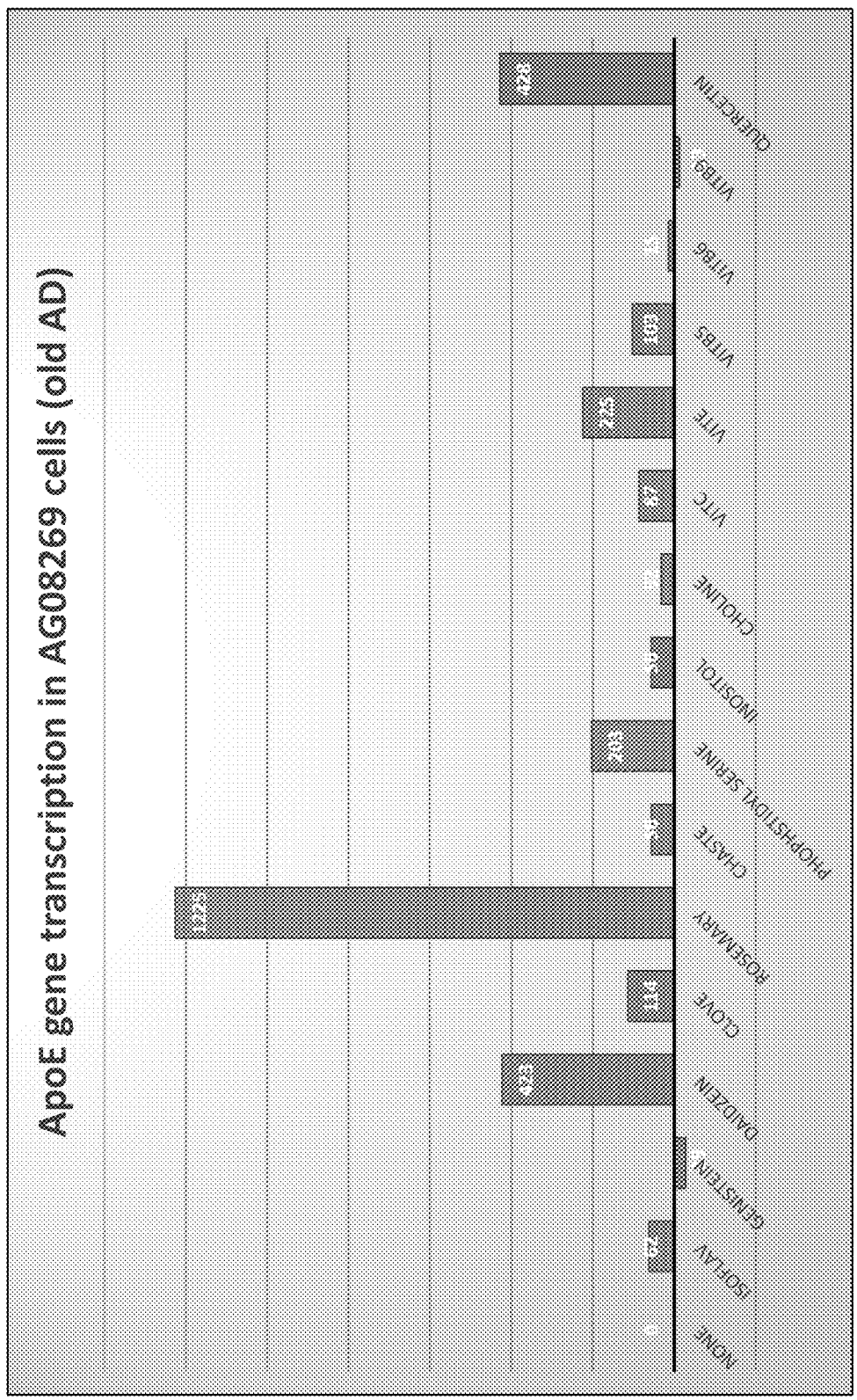
FIG. 15 shows effects of individual components on ApoE gene transcription in fibroblasts cells from old Alzheimer's disease female donor under normal conditions (without IL1β).

FIG. 15 shows effects of individual components on ApoE gene transcription in fibroblasts cells from old Alzheimer's disease female donor under normal conditions (without IL1β). Alzheimer disease (AD) fibroblasts from old female patient were non treated or treated with the individual compounds in concentrations as indicated above. Final concentrations for individual compounds were at 1 ug/ml. Vitamin E, phosphatidyl serine, and inositol were dissolved in DMSO to its final concentration of 0.1% in the cell culture media. Changes in ApoE mRNA expression for these components were corrected for DMSO solvent. After overnight treatment the cells lysates were subjected to RNA isolation, reverse transcribed and the ApoE gene was amplified and quantified by RT-PCR as described in Material and Methods The graph shows the relative number of transcripts of ApoE gene (%) compared to ApoE transcripts in non-treated cells. Each value was standardized to the number of transcripts of Actin B as housekeeping reference gene. These results on FIGS. 14 and 15 show that individual compounds have different effects on ApoE expression under normal and pro-inflammatory conditions (presence of Il1b). Under normal conditions both the isoflavones and choline significantly increased ApoE transcript, while genistein and quercetin had lowering effect. Under pro-inflammatory conditions, most compounds had ApoE increasing effects with Dandzein, rosemary and quercetin being most significant and slight lowering effect was seen with genistein.

Figure 16:
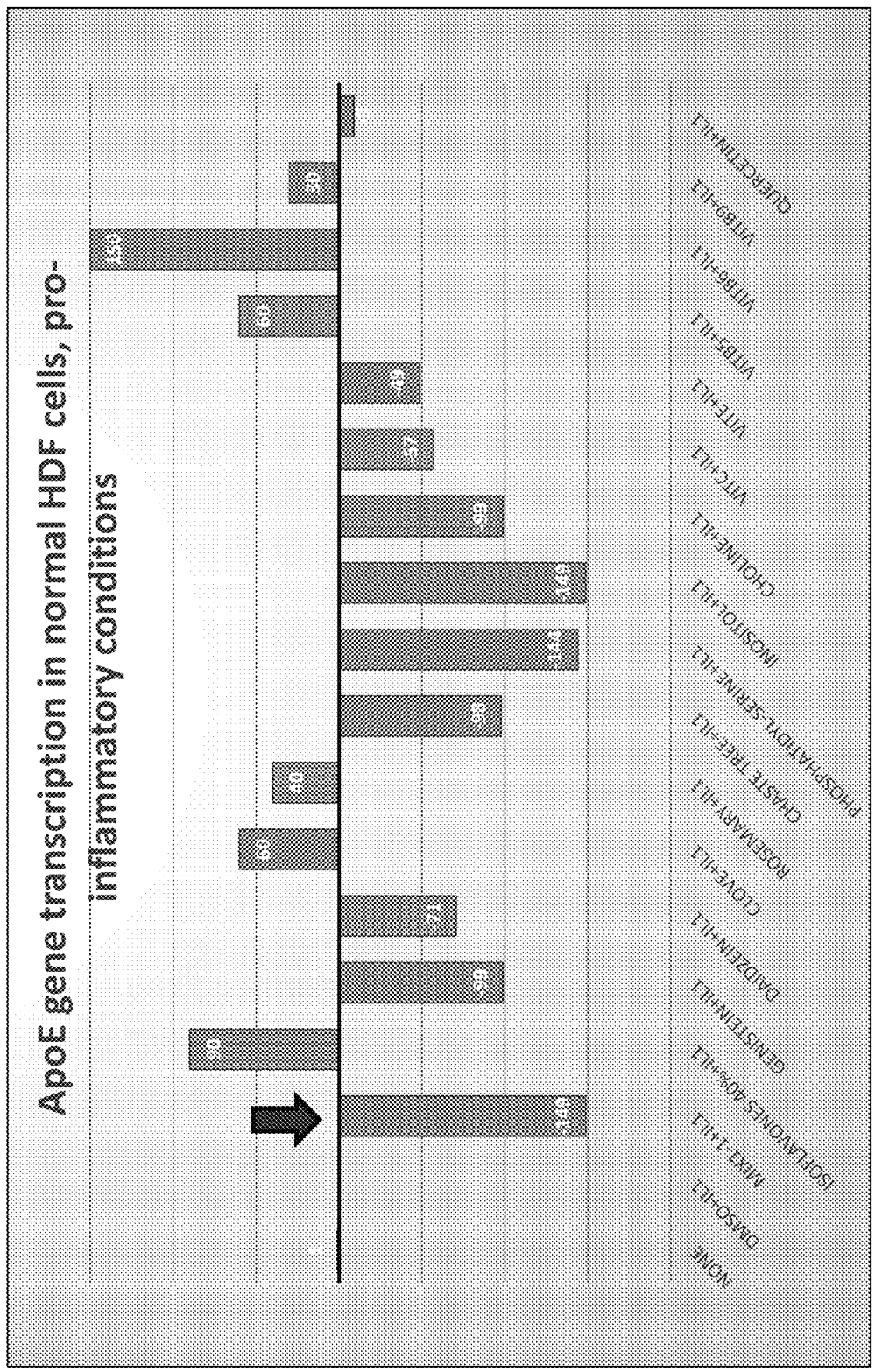
FIG. 16 shows effects of individual components on ApoE gene transcription in NHDF under pro-inflammatory conditions (with IL1β).

FIG. 16 shows effects of individual components on ApoE gene transcription in NHDF under pro-inflammatory conditions (with IL1β). Normal human fibroblasts (HHDF) were grown in DMEM media and non-treated or exposed to IL1b and various individual compounds as indicated above. After overnight treatment the cells lysates were subjected to RNA isolation, reverse transcribed and the ApoE gene was amplified and quantified by RT-PCR. The graph shows the relative number of transcripts of ApoE gene (%) compared to ApoE transcripts in non-treated cells. Each value was standardized to the number of transcripts of Actin B as housekeeping reference gene. Results in FIG. 16 shows that in normal fibroblast cells to under pro-inflammatory condition the majority of individual compounds and Mix 1 have ApoE lowering effect. ApoE expression decrease by Mix 1 was comparable to the ones obtained with phosphatidyl choline and inositol. Under normal conditions the Mix 1, Vitamin E and %5 showed a moderate lowering effect. In summary, the Mix 1 had lowering effect on ApoE in normal human fibroblast cells regardless the effects of other test compounds which would suggest a synergistic effect as well as superior effect of these nutrients.

Figure 17:
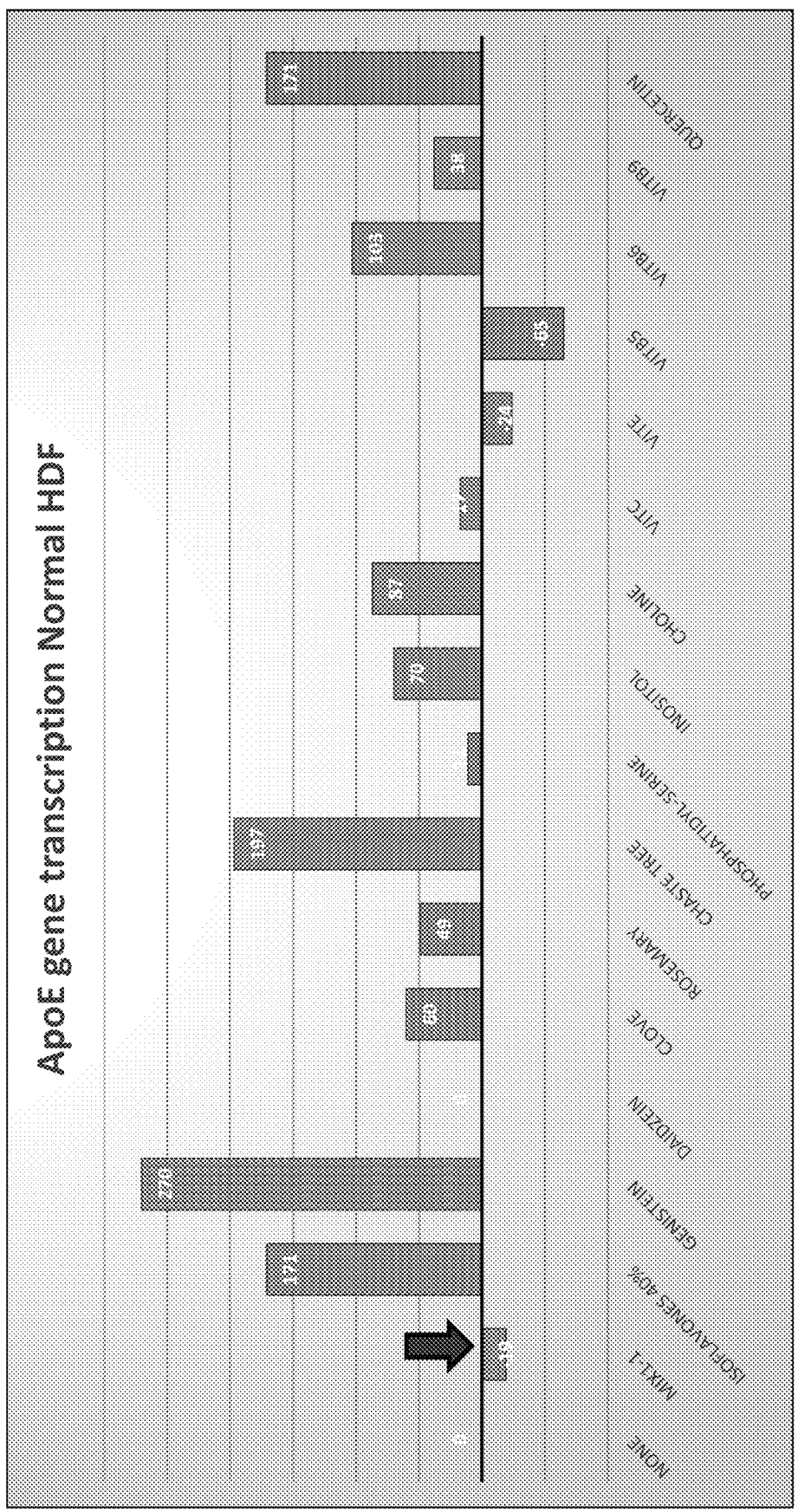
FIG. 17 shows effects of individual components on ApoE gene transcription in NHDF under normal conditions (without IL1β).

FIG. 17 shows effects of individual components on ApoE gene transcription in NHDF under normal conditions (without IL1β). Normal human dermal fibroblasts (NHDF) were non-treated or exposed to various individual compounds as indicated. After overnight incubation the cells lysates were subjected to RNA isolation, reverse transcribed and the ApoE gene was amplified and quantified by RT-PCR. The graph shows the relative number of transcripts of ApoE gene (%) compared to ApoE transcripts in non-treated cells. Each value was standardized to the number of transcripts of Actin B as housekeeping reference gene (LIVAK method of calculation). Our results show that individual compounds and their combination have different effects on ApoE expression under normal and pro-inflammatory conditions (presence of Il1b) in both normal fibroblasts and fibroblasts derived from young and old female AD donors. Since elevated ApoE levels and female gender are considered risk factors for developing Alzheimer's disease or any brain pathology that is effected by elevated Apo E, micronutrients combined in Mix 1 offer important benefits through its inhibitory effect on transcription of ApoE—one of the major risk factors for this disease.

However, in all tests and experimental conditions the Mix 1 had lowering effect on ApoE which implies its beneficial effect in modulating cellular expression of this important marker for brain pathology induced by increased hormones both in its preventive and therapeutic aspects. The said mix's have no cell toxicity, improves bioenergy, provides hormonal support by improved estrogen and progesterone synthesis, has Anti-cancer efficacy: decreased cell growth of breast cancer cells; lowering cancer markers (ApoE and iNOS) in lung cancer cells and Anti-Alzheimer effects: decrease in ApoE as a risk factor associated with Alzheimer's disease in cells derived from young and old female Alzheimer's patients.

The physiological dose is shown in a range after calculating from in vivo studies, that it is suitable for various methods of delivery or consumption. Since different modes of delivery of basic mix or Mix 1 or Mix 2 depend on many factors such as different absorption, severity, individual differences, absorption, but not limited to these. The basic mix, Mix 1 and Mix 2 are formulated using the formula shown in Table 1. The physiological doses are adjusted to suit the formulation for administering the drug and the treatment method chosen based on the female patient ability to get efficient treatment for a said disease. The formulations may be used in combinations as well and are not limited one type.

The physiological dose range for each micronutrient mixture are: Basic mix: Vitamin C in ascorbate form 10 mg-100,000 mg, Vitamin E in D-alpha-tocopherol form 1-3,000 mg, Vitamin B5 1-20,000 mg, Vitamin B6 1-1,000 mg, Folic acid 1-3,000 mcg, Iodine (Kelp) 1-2,000 mcg, Selenium 1-2,000 mcg, Choline 1-5,000 mg, Inositol 1-5000 mg, Phosphatidyl serine 1-1,500 mg, Daidzein 1-1,500 mg, Glycitein 0.1-1,000 mg and Genistein 1-2,500 mg, Mix 1: Vitamin C in ascorbate form 10 mg-100,000 mg, Vitamin E in D-alpha-tocopherol form 1-3,000 mg, Vitamin B5 1-20,000 mg, Vitamin B6 1-1,000 mg, Folic acid 1-3,000 mcg, Iodine (Kelp) 1-2,000 mcg, Selenium 1-2,000 mcg, Choline 1-5,000 mg, Inositol 1-5000 mg, Phosphatidyl serine 1-1,500 mg, Daidzein 1-1,500 mg, Glycitein 0.1-1,000 mg, Genistein 1-2,500 mg, Red clover 1-1,500 mg, Rosemary extract 1-6,000 mg, Chaste tree berry 1-2,000 mg, Mix 2 is: Vitamin C in ascorbate form 10 mg-100,000 mg, Vitamin E in D-alpha-tocopherol form 1-3,000 mg, Vitamin B5 1-20,000 mg, Vitamin B6 1-1,000 mg, Folic acid 1-3,000 mcg, Iodine (Kelp) 1-2,000 mcg, Selenium 1-2,000 mcg, Choline 1-5,000 mg, Inositol 1-5000 mg, Phosphatidyl serine 1-1,500 mg, Daidzein 1-1,500 mg, Glycitein 0.1-1,000 mg, Genistein 1-2,500 mg, Red clover 1-1,500 mg, and Rosemary extract 1-6,000 mg.

Formulations suitable for oral administration for basic mix, Mix 1 and Mix 2 may be in the form of capsules, cachets, pills, tablets, lozenges (using a flavored bases, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin or sucrose and acacia), each containing a predetermined amount of a subject composition as an active ingredient. Subject compositions may also be administered as a bolus, electuary or paste.

When an oral solid drug product is prepared, basic mix or Mix 1 or Mix 2 is mixed with an excipient (and, if necessary, one or more additives such as a binder, a disintegrant, a lubricant, a coloring agent, a sweetening agent, and a flavoring agent), and the resultant mixture is processed through a routine method, to thereby produce an oral solid drug product such as tablets, coated tablets, granules, powder or capsules. Additives may be those generally employed in the art. Examples of excipients include lactate, sucrose, sodium chloride, glucose, starch, calcium carbonate, kaolin, microcrystalline cellulose and silicic acid. Binders include water, ethanol, propanol, simple syrup, glucose solution, starch solution, liquefied gelatin, carboxymethylcellulose, hydroxypropyl cellulose, hydroxypropyl starch, methyl cellulose, ethyl cellulose, shellac, calcium phosphate and polyvinyl pyrrolidone. Disintegrants include dried starch, rice powder, L-leucine, sodium arginate, powdered agar, sodium hydroxy carbonate, calcium carbonate, sodium lauryl sulfate, monoglyceryl stearate and lactose. Lubricants include purified talc, stearic acid salts, borax and polyethylene glycol. Sweetening agents include sucrose, orange peel, citric acid and tartaric acid.

When a liquid drug product for oral administration is prepared, basic mix or Mix 1 or Mix 2 is mixed with an additive such as a sweetening agent, a buffer, a stabilizer, or a flavoring agent, and the resultant mixture is processed through a routine method, to produce an orally administered liquid drug product such as an internal solution medicine, syrup or elixir. Examples of the sweetening agent include vanillin; examples of the buffer include sodium citrate; and examples of the stabilizer include tragacanth, acacia, and gelatin.

For the purposes of transdermal (e.g., topical) administration for all three mixes, dilute sterile, aqueous or partially aqueous solutions (usually in about 0.1% to 5% concentration), otherwise similar to the above parenteral solutions, may be prepared with basic mix or Mix 1 or Mix 2.

Formulations containing basic mix or Mix 1 or Mix 2 for rectal or vaginal administration may be presented as a suppository, which may be prepared by mixing a subject composition with one or more suitable non-irritating carriers, comprising, for example, cocoa butter, polyethylene glycol, a suppository wax or a salicylate, which is solid at room temperature, but liquid at body temperature and, therefore, will melt in the appropriate body cavity and release the encapsulated compound(s) and composition(s). Formulations that are suitable for vaginal administration also include pessaries, tampons, creams, gels, pastes, foams or spray formulations containing such carriers as are known in the art to be appropriate.

A targeted-release portion for capsules containing basic mix or Mix 1 or Mix 2 can be added to the extended-release system by means of either applying an immediate-release layer on top of the extended release core; using coating or compression processes, or in a multiple-unit system such as a capsule containing extended- and immediate-release beads.

When used with respect to a basic mix or Mix 1 or Mix 2, the term "sustained release" is art recognized. For example, a therapeutic composition that releases a substance over time may exhibit sustained-release characteristics, in contrast to a bolus type administration in which the entire amount of the substance is made biologically available at one time. In particular embodiments, upon contact with body fluids, including blood, spinal fluid, mucus secretions, lymph or the like, one or more of the pharmaceutically acceptable excipients may undergo gradual or delayed degradation (e.g., through hydrolysis), with concomitant release of any material incorporated therein, e.g., a therapeutic and/or biologically active salt and/or composition, for a sustained or extended period (as compared with the release from a bolus). This release may result in prolonged delivery of therapeutically effective amounts of any of the therapeutic agents disclosed herein.

Current efforts in the area of drug delivery include the development of targeted delivery, in which the drug is only active in the target area of the body (for example, mucous membranes such as in the nasal cavity), and sustained-release formulations, in which the basic mix or Mix 1 or Mix 2 is released over a period of time in a controlled manner from a formulation. Types of sustained release formulations include liposomes, drug-loaded biodegradable microspheres and basic mix or Mix 1 or Mix 2 polymer conjugates.

Delayed-release dosage formulations are created by coating a solid dosage form with a film of a polymer, which is insoluble in the acid environment of the stomach, but soluble in the neutral environment of the small intestine. The delayed-release dosage units can be prepared, for example, by coating a basic mix or Mix 1 or Mix 2 with a selected coating material. The basic mix or Mix 1 or Mix 2 may be a tablet for incorporation into a capsule, a tablet for use as an inner core in a "coated core" dosage form, or a plurality of drug-containing beads, particles or granules, for incorporation into either a tablet or a capsule. Preferred coating materials include bioerodible, gradually hydrolysable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract, or slowly erode as the dosage form passes through the gastrointestinal tract, while enzymatically degradable polymers are degraded by bacterial enzymes present in the lower gastrointestinal tract, particularly in the colon. Alternatively, a delayed-release tablet may be formulated by dispersing a drug within a matrix of a suitable material such as a hydrophilic polymer or a fatty compound. Suitable hydrophilic polymers include, but are not limited to, polymers or copolymers of cellulose, cellulose ester, acrylic acid, methacrylic acid, methyl acrylate, ethyl acrylate and vinyl or enzymatically degradable polymers or copolymers as described above. These hydrophilic polymers are particularly useful for providing a delayed-release matrix. Fatty compounds for use as a matrix material include, but are not limited to, waxes (e.g., carnauba wax) and glycerol tristearate. Once the active ingredient is mixed with the matrix material, the mixture can be compressed into tablets.

A pulsed-release dosage is one that mimics a multiple dosing profile without repeated dosing, and typically allows at least a twofold reduction in dosing frequency as compared with the drug presented as a conventional dosage form (e.g., as a solution or prompt drug-releasing, conventional solid dosage form). A pulsed-release profile is characterized by a time period of no release (lag time) or reduced release, followed by rapid drug release. These can be formulated for critically ill patients using the instant basic mix or Mix 1 or Mix 2.

The phrases "parenteral administration" and "administered parenterally" as used herein refer to modes of administration other than enteral and topical, such as injections, and include without limitation intravenous, intramuscular, intrapleural, intravascular, intrapericardial, intra-arterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

Certain basic mix or Mix 1 or Mix 2 disclosed herein, suitable for parenteral administration, comprise one or more subject compositions in combination with one or more pharmaceutically acceptable sterile, isotonic, aqueous, or non-aqueous solutions, dispersions, suspensions or emulsions, or sterile powders, which may be reconstituted into sterile injectable solutions or dispersions just prior to use, and which may contain antioxidants, buffers, bacteriostats, solutes that render the formulation isotonic within the blood of the intended recipient, or suspending or thickening agents.

When an injection product is prepared, basic mix or Mix 1 or Mix 2 is mixed with an additive such as a pH regulator, a buffer, a stabilizer, an isotonicity agent or a local anesthetic, and the resultant mixture is processed through a routine method, to thereby produce an injection for subcutaneous injection, intramuscular injection, or intravenous injection. Examples of the pH regulator or buffer include sodium citrate, sodium acetate and sodium phosphate; examples of the stabilizer include sodium pyrosulfite, EDTA, thioglycolic acid, and thiolactic acid; examples of the local anesthetic include procaine hydrochloride and lidocaine hydrochloride; and examples of the isotonicity agent include sodium chloride and glucose.

The phrase "pharmaceutically acceptable" is art recognized. In certain embodiments, the term includes compositions, polymers and other materials and/or dosage forms that are within the scope of sound medical judgment, suitable for use in contact with the tissues of mammals, both human beings and animals, without excessive toxicity, irritation, allergic response or other problem or complication, commensurate with a reasonable benefit-risk ratio.

The phrase "pharmaceutically acceptable carrier" is art recognized, and includes, for example, pharmaceutically acceptable materials, compositions or vehicles, such as a liquid or solid filler, diluent, solvent or encapsulating material involved in carrying or transporting any subject composition from one organ or portion of the body, to another organ or portion of the body. Each carrier must be "acceptable" in the sense of being compatible with the other ingredients of a subject composition, and not injurious to the patient. In certain embodiments, a pharmaceutically acceptable carrier is non-pyrogenic. Some examples of materials that may serve as pharmaceutically acceptable carriers include: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the basic mix or Mix 1 or Mix 2s described herein are formulated in a manner such that said compositions will be delivered to a mammal in a therapeutically effective amount, as part of a prophylactic, or therapeutic treatment to facilitate relaxation of organs build with smooth muscle cells and as such to relax the blood vessels and over the high blood pressure, relax the respiratory pathways important in asthma, relax uterus important in PMS, relax uterine track or gallbladder important in kidney or gallbladder stone all with or without prescribed pharmaceutical drug.

In certain embodiments, the dosage of the basic mix or Mix 1 or Mix 2s, which may be referred to as therapeutic composition provided herein, may be determined by reference to the plasma concentrations of the therapeutic composition or other encapsulated materials. For example, the blood pressure or lung function may be tested for determining the effect of micronutrient treatment in a mammal.

The therapeutic basic mix or Mix 1 or Mix 2 provided by this application may be administered to a subject in need of treatment by a variety of conventional routes of administration, including orally, topically, parenterally, e.g., intravenously, subcutaneously or intramedullary. Further, the therapeutic compositions may be administered intranasally, as a rectal suppository, or using a "flash" formulation, i.e., allowing the medication to dissolve in the mouth without the need to use water. Furthermore, the compositions may be administered to a subject in need of treatment by controlled-release dosage forms, site-specific drug delivery, transdermal drug delivery, patch-mediated drug delivery (active/passive), by stereotactic injection, or in nanoparticles.

Expressed in terms of concentration, an active ingredient can be present in the therapeutic compositions of the present invention for localized use via the cutis, intranasally, pharyngolaryngeally, bronchially, intravaginally, rectally or ocularly.

For use as aerosols, the active ingredients can be packaged in a pressurized aerosol container together with a gaseous or liquefied propellant, for example dichlorodifluoromethane, carbon dioxide, nitrogen, propane and the like, with the usual adjuvants such as cosolvents and wetting agents, as may be necessary or desirable. The most common routes of administration also include the preferred transmucosal (nasal, buccal/sublingual, vaginal, ocular and rectal) and inhalation routes.

In addition, in certain embodiments, the subject basic mix or Mix 1 or Mix 2 of the present application may be lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject basic mix or Mix 1 or Mix 2 that may be combined with a carrier material to produce a single dose may vary depending upon the subject being treated and the particular mode of administration.

The therapeutically acceptable amount described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may, for example, contain 0.005-90% w/w, for instance 0.005-50%, 0.005-5% w/w, or 0.01-1.0% w/w, of medicament relative to the total weight of the formulation.

Examples of suitable aqueous and non-aqueous carriers that may be employed in the basic mix or Mix 1 or Mix 2 include water, ethanol, polyols (such as glycerol, propylene glycol, polyethylene glycol and the like), and suitable mixtures thereof, vegetable oils such as olive oil, and injectable organic esters such as ethyl oleate. Proper fluidity may be maintained, for example by the use of coating materials such as lecithin, by the maintenance of the required particle size in the case of dispersions, and by the use of surfactants.

INDUSTRIAL USE

Thus, in this study we prove that basic mix or Mix 1 or Mix 2 plays a decisive role in regulating the estrogen related diseases in individuals. With optimum combination of natural ingredients and micronutrients the estrogen related diseases is controlled at a significant level.

What is claimed is:

1. A micronutrient mixture, consisting of:
Vitamin C in ascorbate form, Vitamin E in D-alpha-tocopherol form, Vitamin B5, Vitamin B6, Folic acid, Iodine, Selenium, Choline, Inositol, Phosphatidyl serine, Soy extract containing Daidzein, Glycitein, Genistein, Red clover, Rosemary extract, and Chaste tree berry and optionally one or a combination of pharmaceutically acceptable carriers, excipient, liquefied propellant, buffer, pH regulator, stabilizer, coating or flavoring agent, wherein the micronutrient mixture is formulated as a tablet, coated tablet, capsule, pill, intranasal, lozenges, emulsion, pastilles, suppository, paste or injectable solution.

2. A method of improving female health due to estrogen hormone variations, comprising;
administering to a female in need thereof a micronutrient mixture, wherein the micronutrient mixture comprises Vitamin C in ascorbate form in an amount of 10 mg-100,000 mg, Vitamin E in D-alpha-tocopherol form in an amount of 1 mg-3,000 mg, Vitamin B5 in an amount of 1 mg-20,000 mg, Vitamin B6 in an amount of 1 mg-1,000 mg, Folic acid in an amount of 1 mcg-3,000 mcg, Iodine in an amount of 1 mcg-2,000 mcg, Selenium in an amount of 1 mcg-2,000 mcg, Choline in an amount of 1 mg-5,000 mg, Inositol in an amount of 1 mg-5000 mg, Phosphatidyl serine in an amount of 1 mg-1,500 mg, Daidzein in an amount of 1 mg-1,500 mg, Glycitein in an amount of 0.1 mg-1,000 mg, Genistein in an amount of 1 mg-2,500 mg, Red clover in an amount of 1 mg-1,500 mg, Rosemary extract in an amount of 1 mg-6,000 mg, and Chaste tree berry in an amount of 1 mg-2,000 mg and optionally one or a combination of pharmaceutically acceptable carriers, excipient, liquefied propellant, buffer, pH regulator, stabilizer, coating or flavoring agent, wherein the micronutrient mixture is formulated as a tablet, coated tablet, capsule, pill, intranasal, lozenges, emulsion, pastilles, suppository, paste or injectable solution.

3. The method of claim 2, further comprising;
decreasing estrogen dependent breast cancer cells proliferation in females.

4. The method of claim 2, further comprising;
decreasing expression of cancer promoting cellular markers in lung cancer cells in females.

5. The method of claim 2, further comprising;
increasing bioenergy production in cells.

6. The method of claim 2, further comprising;
increasing synthesis of 17 beta Estradiol and progesterone in ovarian granulosa cells.

7. A method of using a micronutrient mixture, comprising;
administering to a female in need thereof a micronutrient mixture, wherein the micronutrient mixture comprises Vitamin C in ascorbate form, Vitamin E in D-alpha-tocopherol form, Vitamin B5, Vitamin B6, Folic acid, Iodine, Selenium, Choline, Inositol, Phosphatidyl serine, Daidzein, Glycitein, Genistein, Red clover, Rosemary extract, and Chaste tree berry and optionally one or a combination of pharmaceutically acceptable carriers, excipient, liquefied propellant, buffer, pH regulator, stabilizer, coating or flavoring agent, wherein the micronutrient mixture is formulated as a tablet, coated tablet, capsule, pill, intranasal, lozenges, emulsion, pastilles, suppository, paste or injectable solution; and treating a female suffering from cancer by reducing the proliferation of cancer cells.

8. The method of claim 7, wherein the micronutrient mixture consists of the Vitamin C in ascorbate form in an amount of 10 mg-100,000 mg, Vitamin E in D-alpha-tocopherol form in an amount of 1 mg-3,000 mg, Vitamin B5 in an amount of 1 mg-20,000 mg, Vitamin B6 in an amount of 1 mg-1,000 mg, Folic acid in an amount of 1 mcg-3,000 mcg, Iodine in an amount of 1 mcg-2,000 mcg, Selenium in an amount of 1 mcg-2,000 mcg, Choline in an amount of 1 mg-5,000 mg, Inositol in an amount of 1 mg-5000 mg, Phosphatidyl serine in an amount of 1 mg-1,500 mg, Daidzein in an amount of 1 mg-1,500 mg, Glycitein in an amount of 0.1 mg-1,000 mg, Genistein in an amount of 1 mg-2,500 mg, Red clover in an amount of 1 mg-1,500 mg, Rosemary extract in an amount of 1 mg-6,000 mg, and Chaste tree berry in an amount of 1 mg-2,000 mg.

9. The method of claim 8, further comprising;
decreasing estrogen dependent breast cancer cells proliferation in females.

10. The method of claim 8, further comprising;
decreasing expression of cancer promoting cellular markers in lung cancer cells in females.

11. The method of claim 8, further comprising;
increasing bioenergy production in cells.

12. The method of claim 8, further comprising;
increasing synthesis of 17 beta Estradiol and progesterone in ovarian granulosa cells.

* * * * *